US012678458B2

(12) United States Patent
Baiti

(10) Patent No.: US 12,678,458 B2
(45) Date of Patent: Jul. 14, 2026

(54) ANTISEPTIC COMPOSITION

(71) Applicant: BOBS SILVER, Paris (FR)

(72) Inventor: Sadek Baiti, Fougeres (FR)

( * ) Notice: Subject to any disclaimer, the term of this patent is extended or adjusted under 35 U.S.C. 154(b) by 540 days.

(21) Appl. No.: 18/251,645

(22) PCT Filed: Nov. 4, 2021

(86) PCT No.: PCT/EP2021/080689
§ 371 (c)(1),
(2) Date: May 3, 2023

(87) PCT Pub. No.: WO2022/096605
PCT Pub. Date: May 12, 2022

(65) Prior Publication Data
US 2023/0405044 A1 Dec. 21, 2023

(30) Foreign Application Priority Data

Nov. 4, 2020 (FR) ...................................... 2011337
Jun. 24, 2021 (FR) ...................................... 2106735

(51) Int. Cl.
| | |
|---|---|
| A61K 33/38 | (2006.01) |
| A61K 35/644 | (2015.01) |
| A61K 36/185 | (2006.01) |
| A61K 36/28 | (2006.01) |
| A61P 31/00 | (2006.01) |
| A61P 31/04 | (2006.01) |
| A61P 31/10 | (2006.01) |

(52) U.S. Cl.
CPC ........... *A61K 33/38* (2013.01); *A61K 35/644* (2013.01); *A61K 36/185* (2013.01); *A61K 36/28* (2013.01); *A61P 31/04* (2018.01); *A61P 31/10* (2018.01)

(58) Field of Classification Search
CPC .................................................... A61K 33/38
See application file for complete search history.

(56) References Cited

U.S. PATENT DOCUMENTS

| | | | |
|---|---|---|---|
| 9,662,356 B1 | 5/2017 | Dubourdieu et al. | |
| 2010/0323013 A1 | 12/2010 | Bonn et al. | |
| 2011/0104302 A1* | 5/2011 | Kiani ..................... A61K 45/06 | |
| | | | 424/618 |
| 2018/0235232 A1* | 8/2018 | Moeller ................. A61K 31/60 | |

FOREIGN PATENT DOCUMENTS

| | | | |
|---|---|---|---|
| CN | 101757246 A | 6/2010 | |
| EP | 0870507 A1 | 10/1998 | |
| WO | 02094300 A1 | 11/2002 | |
| WO | 2005120173 A2 | 12/2005 | |
| WO | 2008104076 A1 | 9/2008 | |
| WO | WO2012035082 * | 3/2012 | |
| WO | 2019209227 A2 | 10/2019 | |
| WO | WO2019199260 * | 10/2019 | |

OTHER PUBLICATIONS

Cleveland Clinic. Camphylobacter infection. Retrieved (Year: 2025).*
Hussain et al. Breakthrough COVID-19 Infections-Analyzing our eperience. (Year: 2023).*
Vedantu. Human Bacterial Diseases. Retrieved (Year: 2025).*
Azo Materials (Colloids—Definition, Types and Formation of Colloids) (Year: 2006).*
Rex, J.H et al., "M38-A2 Reference method for Broth Dilution Antifungal Susceptibility Testing of Filamentous Fungi; Approved Standard-Second Edition", Clinical and Laboratory Standards Institute (2008).
Melvin P. Weinstein, MD, et al., Performance Standards for Antimicrobial Susceptibility Testing, M100—30th ed., Clinical and Laboratory Standards Institute, Jan. 2020.
Franklin R. Cockerill, III, MD, et al., Performance Standards for Antimicrobial Disk Susceptibility Tests; Approved Standard-Eleventh Edition, M02-A11, vol. 32, No. 1, Clinical and Laboratory Standards Institute, Jan. 2012.
A.W. Bauer, MD, et al., Antibiotic Susceptibility Testing by a Standardized Single Disk Method, The American Journal of Clinical Pathology, vol. 45, No. 4, 1966, pp. 493-496.
Antibiotic Sensitivity Testing, British Medical Journal, 1971, p. 416.

* cited by examiner

*Primary Examiner* — Sarah Alawadi
(74) *Attorney, Agent, or Firm* — DECODE Legal Inc.

(57) ABSTRACT

A formulation for use as a drug comprises at least colloidal silver, *Sambucus nigra* extract, *Primulae flos* cum calycibus extract and/or *Hypericum perforatum* extract, and *Pelargonium sidoides* extract. Preferentially, this formulation is used for prophylaxis and/or for antiviral, antibacterial and antifungal treatment. Even more preferentially, the formulation is an antifungal and antibacterial cream.

12 Claims, No Drawings

ANTISEPTIC COMPOSITION

The invention relates to a formulation for use as a drug comprising at least colloidal silver, *Sambucus nigra* extract, *Primulae flos* cum calycibus extract and/or *Hypericum perforatum* extract, and *Pelargonium sidoides* extract. Preferentially, said formulation is used for prophylaxis and/or for antiviral, antibacterial and antifungal treatment. Even more preferentially, said formulation is an antifungal and antibacterial cream.

The invention relates to the field of antifungal, antiviral and antibacterial treatments.

PRIOR ART

The healing properties of silver were already known in Ancient Greece: it was known that families who used silver cutlery to eat were less prone to infection. Silver has significant antimicrobial properties as the presence of one part of elemental silver per 100 million in a solution is enough to produce effective antimicrobial action. It is also established that silver ions or free radicals are an active antimicrobial agent.

To make silver water-soluble, a colloidal ionic form (a suspension of extremely fine silver particles in water) must be used, obtained for the first time in 1920 through hydrolysis wherein two pure silver electrodes, submerged in demineralised or distilled water, which were subjected to a potential difference, were used.

Before the advent of antibiotics in 1938, the colloidal silver produced using this process was prescribed for a wide variety of diseases and infections: it had been established that it was efficient against 650 different pathogenic agents.

Colloidal silver boosts the immune system, as it acts as a catalyst by deactivating the specific enzymes necessary for the metabolism of many bacterial, fungal and viral species.

This success is due to the fact that it is a safe antiseptic. When used as a colloid, silver is absorbed very slowly by the tissue so as not to produce any toxic effects. It can therefore be used orally and be incorporated into preparations that can be taken daily by adults and children without any risks of any intolerance, even following intake over an extended period of time.

Colloidal silver is primarily used as an antiseptic in dermatology to treat certain types of skin lesions. It is also known for its application as a water purifier and a preservative in the cosmetic industry.

However, colloidal silver is not efficient against all fungi, viruses and bacteria.

Currently, and increasingly so since the outbreak of the global pandemic related to the SARS-CoV-2 virus, there is a persistent need for an alternative to existing formulations that would be effective against all current and future pathogenic viruses, fungi and bacteria.

There is also a persistent need for alternatives in topical antifungal and/or antibacterial treatments.

Furthermore, there is also a need to identify new antibiotic formulations, to treat antibiotic-resistant patients.

Unexpectedly, the applicant discovered that combining colloidal silver with several plant extracts produced an effective formulation for prophylaxis and for antiviral, antibacterial and antifungal treatment.

DESCRIPTION

Therefore, according to a first aspect, the invention relates to a formulation for use as a drug comprising:

Colloidal silver;

*Sambucus nigra* extract;

*Primulae flos* cum calycibus extract and/or *Hypericum perforatum* extract;

*Pelargonium sidoides* extract.

According to the invention, colloidal ionic silver is meant as extremely fine silver particles suspended in water.

Preferentially, said colloidal silver has a particle size between 0.1 and 30 nanometres.

Preferentially, said formulation for use according to the invention comprises:

Between 20 and 250 mg of colloidal silver per litre of formulation.

By convention, it is generally considered that 1 mg of silver is equivalent to 1 ppm in a solution of 1 litre, i.e. 20 to 250 mg per litre of solution.

*Sambucus nigra*, also known as black elderberry, is a plant that grows as a shrub in the Caprifoliaceae family. Extracts from this plant can be derived from its flowers or fruit and can be dry, aqueous and/or alcohol extracts.

Preferentially, said formulation for use according to the invention comprises:

Between 0.3 and 5% by weight of the *Sambucus nigra* extract formulation.

*Primulae flos* cum calycibus (Primrose flowers with calyx) is a perennial herbaceous plant in the Primulaceae family. Said extracts are derived from the plant's crushed flowers and/or calyx, optionally in water and/or alcohol. These extracts can also be dry extracts.

Preferentially, said formulation for use according to the invention comprises:

Between 1 and 9% by weight of the *Primulae flos* cum calycibus extract formulation.

*Hypericum perforatum*, more commonly known as Saint John's Wort, is a perennial herbaceous plant in the *Clusiaceae* family. Said extracts are derived from the plant or flower tops that can be crushed, optionally in water and/or alcohol.

Preferentially, said formulation for use according to the invention comprises:

Between 0.5 and 11% by weight of the *Hypericum perforatum* extract formulation.

*Pelargonium sidoides*, or Umckaloabo, is a plant native from South Africa. Extracts from this plant can come as dry, aqueous and/or alcohol extracts from the roots and other parts of the plant.

Preferentially, said formulation for use according to the invention comprises:

Between 1 and 6% by weight of the *Pelargonium sidoides* extract formulation.

According to an embodiment, said formulation for use according to the invention comprises:

Between 20 and 250 mg of colloidal silver per litre of formulation.

Between 0.3 and 5% by weight of the *Sambucus nigra* extract formulation;

Between 1 and 9% by weight of the *Primulae flos* cum calycibus extract formulation and/or between 0.5 and 11% by weight of the *Hypericum perforatum* extract formulation;

Between 1 and 6% by weight of the *Pelargonium sidoides* extract formulation.

According to an embodiment, said formulation for use according to the invention further comprises:

Ionic silver;

According to the invention, ionic silver is meant as silver whose particles have been dissolved in water, as opposed to colloidal silver where said particles are suspended in water.

According to an embodiment, said formulation for use according to this last embodiment comprises:

Between 20 and 250 mg of total silver per litre of formulation, distributed as i. Between 70 and 99.99% by total weight of silver, colloidal silver;

ii. Between 0.01 and 30% by total weight of silver, ionic silver.

According to the invention, total silver is meant as the entire silver content in the formulation according to the invention, irrespective of its form.

According to an embodiment, said formulation for use comprises:

Between 20 and 250 mg of total silver per litre of formulation, distributed as i. Between 70 and 99.99% by total weight of silver, colloidal silver;

ii. Between 0.01 and 30% by total weight of silver, ionic silver;

Between 0.3 and 5% by weight of the *Sambucus nigra* extract formulation;

Between 1 and 9% by weight of the *Primulae flos* cum calycibus extract formulation and/or between 0.5 and 11% by weight of the *Hypericum perforatum* extract formulation;

Between 1 and 6% by weight of the *Pelargonium sidoides* extract formulation.

According to an embodiment, said formulation for use according to the invention further comprises:

*Echinacea* extract, and/or

*Propolis* and/or

*Artemisia* extract and/or

*Allium sativum* extract.

*Echinacea* is a genus of plant in the Asteraceae family. Said extracts come as dry, aqueous and/or alcohol extracts, produced from the root, whole plant or aerial parts.

Preferentially, said formulation for use according to the invention comprises:

Between 0.01 and 8% by weight of the *Echinacea* extract formulation.

*Allium sativum*, more commonly referred to as "Garlic", is a perennial plant. Extracts can be dry, aqueous and/or alcohol, or aged garlic extract.

Preferentially, said formulation for use according to the invention comprises:

Between 0.01 and 10% by weight of the *Allium sativum* extract formulation.

"*Propolis*" is a by-product of plant resins and exudates, which may be secreted by plants or produced by bees from plant resin and wax. As *propolis* depends on the plant species from which it is produced, standardised *propolis* is produced, often determined by its colour. Preferentially, yellow, green or red *propolis* is used. Said *propolis* can be presented as dry, purified, aqueous and/or alcohol extract.

Preferentially, said formulation for use according to the invention comprises:

Between 0.01 and 7% by weight of the *propolis* formulation.

*Artemisia* or Mugwort is a plant species comprising herbaceous plants and shrubs with pennate leaves. Preferentially, the species used according to the invention is

*Artemisia annua*. It is a herbaceous ramified aromatic plant. Extracts from this plant can be derived from the whole plant or its aerial parts and be dry, aqueous and/or alcohol extracts.

Preferentially, said formulation for use according to the invention comprises:

Between 0.5 and 3% by weight of the *Artemisia* extract formulation.

Preferentially, said formulation for use according to the invention comprises:

Between 0.01 and 8% by weight of the *Echinacea* extract formulation, and/or

Between 0.01 and 7% by weight of the *Propolis* formulation, and/or

Between 0.5 and 3% by weight of the *Artemisia* extract formulation, and/or

Between 0.01 and 10% by weight of the *Allium sativum* extract formulation.

Preferentially according to the invention, said formulation for use according to the invention comprises at least another dermatologically and/or pharmaceutically acceptable agent.

According to an embodiment, said formulation for use according to the invention is intended for use for prophylaxis and/or antiviral, antibacterial and antifungal treatment.

According to an embodiment, said formulation for use according to the invention is intended for use for prophylaxis and/or antiviral treatment.

According to an embodiment, said formulation for use according to the invention is intended for use for prophylaxis and/or antibacterial treatment.

According to an embodiment, said formulation for use according to the invention is intended for use for prophylaxis and/or antifungal treatment.

According to an embodiment, said formulation for use according to the invention is intended for use for prophylaxis and/or antibacterial and antifungal treatment.

Preferentially, said formulation for use according to the invention, can be administered by oral, intravenous, subcutaneous, nasal, ophthalmic, auricular, rectal, vaginal, respiratory routes or by application on the skin.

Even more preferentially, the oral route can be a tablet, cordial, drinkable solution or suspension, or gel capsule, Even more preferentially, the intravenous route can be a solution.

Even more preferentially, the subcutaneous route can be a solution.

Even more preferentially, the route of application on the skin can be an ointment, cream, patch or gel.

Preferentially, administration is done through the respiratory tract or nasal passages.

Preferentially, said formulation for use according to the invention is administered by respiratory or nasal route, as nasal drops, nasal spray, nasal powder, spray, for example compressed air sprays and/or nasal sprays, or a nebuliser.

Advantageously, when the pharmaceutical formulation is suitable for nasal administration or by the respiratory route, it can advantageously be for bronchopulmonary or sinus purposes.

Preferentially, said formulation for use according to the invention is administered by spray in the nasal passages.

The formulation according to this invention can be administered to a patient on a daily basis, once daily, twice daily, three times daily or more times daily. Preferentially, the formulation of this invention is administered to a patient twice daily and at 12-hour intervals.

According to an embodiment of the invention, said formulation comprises, by weight of formulation:

Pharmaceutical grade purified water: qsf 20 mg Silver in total up to 20% ionic silver and 80% colloidal silver, with a mean particle size of 0.8 nm;

0.9% *Sambucus nigra* extract;

5% *Hypericum perforatum* extract;

1.5% dry *Pelargonium sidoides* extract;

3% dry *Echinacea* extract;

4% purified *Propolis* extract.

According to an embodiment of the invention, said formulation comprises, by weight of formulation:

Pharmaceutical grade purified water: qsf 20 mg Silver in total up to 20% ionic silver and 80% colloidal silver, with a mean particle size of 0.8 nm;

0.9% *Sambucus nigra* extract;

5% dry *Primulae flos* cum calycibus extract;

5% *Hypericum perforatum* extract;

1.5% dry *Pelargonium sidoides* extract;

3% dry *Echinacea* extract;

4% purified *Propolis* extract.

More preferentially, the formulation for use according to the invention is a cream for topical application.

According to an embodiment, said cream for topical application is an antifungal cream.

According to an embodiment, said cream for topical application is an antibacterial cream.

Even more preferentially, said cream for topical application is an antifungal and antibacterial cream.

The formulation for use according to this invention, as an antifungal and/or antibacterial cream for topical application, can be topically administered to a patient on a daily basis, once daily, twice daily, three times daily or more times daily. Preferentially, the formulation of this invention is administered to a patient twice daily and at 12-hour intervals.

According to a different embodiment, said formulation is used as an antibiotic.

Preferentially, said formulation is used as an antibiotic to treat antibiotic-resistant patients.

Antibiotic resistance is a phenomenon whereby a pathogenic organism becomes resistant to antibiotics. These organisms change and develop defence mechanisms that inhibit the antibiotic treatments. These treatments thus become ineffective.

Preferentially, said formulation for use as antibiotic can be administered by oral, intravenous, subcutaneous, nasal, ophthalmic, auricular, rectal, vaginal, respiratory routes or by application on the skin.

Even more preferentially, the oral route can be a tablet, cordial, drinkable solution or suspension, or gel capsule, Even more preferentially, the intravenous route can be a solution.

Even more preferentially, the subcutaneous route can be a solution.

Even more preferentially, the route of application on the skin can be an ointment, cream, patch or gel.

According to a second aspect, the invention relates to a formulation comprising:

Colloidal silver;

*Sambucus nigra* extract;

*Primulae flos* cum calycibus extract and/or *Hypericum perforatum* extract;

*Pelargonium sidoides* extract.

Preferentially, said formulation according to the invention comprises:

Between 20 and 250 mg of colloidal silver per litre of formulation.

Preferentially, said formulation according to the invention comprises:

Between 0.3 and 5% by weight of the *Sambucus nigra* extract formulation.

Preferentially, said formulation according to the invention comprises:

Between 1 and 9% by weight of the *Primulae flos* cum calycibus extract formulation.

Preferentially, said formulation according to the invention comprises:

Between 0.5 and 11% by weight of the *Hypericum perforatum* extract formulation.

Preferentially, said formulation according to the invention comprises:

Between 1 and 6% by weight of the *Pelargonium sidoides* extract formulation.

According to an embodiment, said formulation comprises:

Between 20 and 250 mg of colloidal silver per litre of formulation;

Between 0.3 and 5% by weight of the *Sambucus nigra* extract formulation;

Between 1 and 9% by weight of the *Primulae flos* cum calycibus extract formulation and/or between 0.5 and 11% by weight of the *Hypericum perforatum* extract formulation;

Between 1 and 6% by weight of the *Pelargonium sidoides* extract formulation.

According to an embodiment, said formulation according to the invention further comprises:

Ionic silver;

According to an embodiment, said formulation according to this last embodiment comprises:

Between 20 and 250 mg of total silver per litre of formulation, distributed as i. Between 70 and 99.99% by total weight of silver, colloidal silver;

ii. Between 0.01 and 30% by total weight of silver, ionic silver.

According to an embodiment, said formulation comprises:

Between 20 and 250 mg of total silver per litre of formulation, distributed as i. Between 70 and 99.99% by total weight of silver, colloidal silver;

ii. Between 0.01 and 30% by total weight of silver, ionic silver;

Between 0.3 and 5% by weight of the *Sambucus nigra* extract formulation;

Between 1 and 9% by weight of the *Primulae flos* cum calycibus extract formulation and/or between 0.5 and 11% by weight of the *Hypericum perforatum* extract formulation;

Between 1 and 6% by weight of the *Pelargonium sidoides* extract formulation.

According to an embodiment, said formulation according to the invention further comprises:

*Echinacea* extract, and/or

*Propolis* and/or

*Artemisia* extract and/or

*Allium sativum* extract.

Preferentially, said formulation according to the invention comprises:

Between 0.01 and 8% by weight of the *Echinacea* extract formulation.

Preferentially, said formulation according to the invention comprises:

Between 0.01 and 10% by weight of the *Allium sativum* extract formulation.

Preferentially, said formulation according to the invention comprises:

Between 0.01 and 7% by weight of the *propolis* formulation.

Preferentially, said formulation according to the invention comprises:

Between 0.5 and 3% by weight of the *Artemisia* extract formulation.

Preferentially, said formulation according to the invention comprises:

Between 0.01 and 8% by weight of the *Echinacea* extract formulation, and/or

Between 0.01 and 7% by weight of the *Propolis* formulation, and/or

Between 0.5 and 3% by weight of the *Artemisia* extract formulation, and/or

Between 0.01 and 10% by weight of the *Allium sativum* extract formulation.

According to an embodiment of the invention, said formulation comprises, by weight of formulation:

Pharmaceutical grade purified water: qsf 20 mg Silver in total up to 20% ionic silver and 80% colloidal silver, with a mean particle size of 0.8 nm;

0.9% *Sambucus nigra* extract;

5% *Hypericum perforatum* extract;

1.5% dry *Pelargonium sidoides* extract;

3% dry *Echinacea* extract;

4% purified *Propolis* extract.

According to an embodiment of the invention, said formulation comprises, by weight of formulation:

Pharmaceutical grade purified water: qsf 20 mg Silver in total up to 20% ionic silver and 80% colloidal silver, with a mean particle size of 0.8 nm;

0.9% *Sambucus nigra* extract;

5% dry *Primulae flos* cum calycibus extract;

5% *Hypericum perforatum* extract;

1.5% dry *Pelargonium sidoides* extract;

3% dry *Echinacea* extract;

4% purified *Propolis* extract.

According to a third aspect, the invention relates to the use of the formulation according to the second aspect of the invention to sanitize a surface.

In this invention, surface sanitization is meant as applying formulation according to the invention to inert surfaces to obtain an anti-fungal and/or antiviral and/or antibacterial effect on the surface to which it is applied.

The surfaces on which this formulation is used can generally be found wherever it may be necessary to sanitize a surface or objects or devices, for example in the food industry, stores, restaurants, a medical environment or even in private homes.

Preferentially according to the invention, said surface is a surface in a medical environment, for example in a medical practice, a hospital, a test laboratory, a veterinary clinic.

"Surface in a medical environment" in particular refers to floors, walls, benches and medical instruments.

EXAMPLES

Example 1: Formulation Example

For 100 ml of formulation, the formulation comprises:

20 mg Silver in total up to 20% ionic silver and 80% colloidal silver, with a mean particle size of 0.8 nm.

0.9% *Sambucus nigra* extract

5% dry *Primulae flos* cum calycibus and/or *Hypericum perforatum* extract 1.5% dry *Pelargonium sidoides* extract 3% dry *Echinacea* extract 4% purified *Propolis* extract.

Example 2: Antibacterial Activity of the Formulation of Example 1

The antibacterial activity was tested by monitoring the concentrations of cultivable *Staphylococcus aureus* in vitro after seeding strains tested and placed in contact with the formulation of example 1.

The concentrations expressed in CFU/ml were measured for 1, 3 and 24-hour periods, and enabled a bactericidal effect to be characterised.

The findings showed that the formulation has a bactericidal effect.

Example 3: Antibacterial Effect of the Formulation of Example 1

The formulation of example 1 was tested according to the test assessing the potential activity against HRV-A16 (a rhinovirus responsible for colds) on a culture of entirely differentiated epithelial cells from human respiratory tracts. The formulations were first applied before the infection for one hour and the replication was performed for 4 hours. 3 rinsing steps with the formulations were carried out. The rest was collected and the RNA was assayed after cell lysis. The same collection step was performed 24 hours later and the same assay step was performed. The percentage expresses the changes in the viral RNA, resulting in a percent inhibition of HRV-A16 replication, leading to antiviral efficacy. The formulation according to example 1 was tested against rupintrivir (a well-known antiviral compound delivering an almost complete response). The results were greater for the formulation according to example 1.

Example 4: Antifungal Activity of the Formulation of Example 1

A strain of *Scytalidium dimidiatum* was obtained by separating and identifying the stratum corneum in patients with superficial mycosis. The fungi precultivated on an SDA medium were suspended in a sterile saline solution containing 0.1% (p/v) Tween 80 and the suspension was filtered through a gauze to collect the arthrospores. It was suspended in a sterile saline solution containing 0.1% (p/v) Tween 80, then added to a medium containing 20% Alamar blue with $2 \times 10$ 4 cells/ml to create a fungal inoculum solution.

The formulation according to example 1 was used, as well as luliconazole.

Trial Method

The minimum inhibitory concentration (MIC) was measured using a broth microdilution process. Meaning that the RPMI1640 medium (Sigma-Aldrich) was buffered with 0.165 M morpholine propane sulfonic acid (MOPS, Wako Pure Chemical Industries, Ltd.) with a pH 7.0, and a given quantity of a solution of the formulation according to example 1 or luliconazole was added to prepare two-fold serial dilutions within the 0.00098-4 µg/mL range. 100 µl were added to a 96-well microplate, then a solution of fungal inoculum (100 µl, final fungal concentration to be added: $1.0 \times 10^4$ cells/ml) and the mixture was cultivated at 35° C. An Alamar blue reagent was added to the growth medium beforehand (final concentration of the addition: 10%) and, when the Alamar blue reagent in the control growth group without the drug turned from blue to red, the culture was discontinued and the absorbance (differential optical density at 570 nm on the basis of 590 nm was used as a benchmark) was measured. The minimum concentration of the formulation according to example 1 or luliconazole which inhibited the growth of the fungus in the control growth group by 80% or over was used as MIC. The concentration being the MIC (MIC90) in 9 strains out of the 10 measured strains (90%) was determined.

Reference documents for the measurement method: Takako Shinoda et al.: opinion issued by the Committee for Clinical Laboratory Standards of the Japanese Society for Medical Mycology (1995-1997), Method for antifungal susceptibility testing of filamentous fungus, Medical Mycology Journal, 40: 239-257, 1999. Clinical and Laboratory Standards Institute/National Committee for Clinical Laboratory Standards. Reference method for antifungal susceptibility testing of filamentous fungus by dilution in a broth. M38-A2 approved standard. Wayne, PA: National Committee for Clinical Laboratory Standards, 2008.

Findings

The MIC of the formulation according to example 1 was greater than luliconazole, showing a specifically high antifungal activity.

Example 5: In Vivo Antiviral, Antibacterial and Antifungal Efficacy Test

Two groups of 20 patients each, with a viral, fungal and/or bacterial infection were treated with the formulation covered in example 1 or with a saline solution (PLACEBO). The treatment consisted in spraying the formulation of example 1 and PLACEBO twice daily. The treatment was administered for two weeks. The treatment's efficacy was assessed using a total symptom score, in relation with the samples taken with swabs. The scores, assessed at the beginning and end of the treatment with the Student t-test, were used to assign an efficacy score with the same statistical method.

The results showed that the formulation of example 1 had a greater efficacy than the saline solution.

Example 6: Study Protocol of the In Vitro Antimicrobial Activity for the Combination of *Pelargonium sidoides, Sambucus nigra* and *Hypericum perforatum* Extracts with Colloidal Silver These studies were conducted to test and assess the antimicrobial activity of *Pelargonium sidoides, Hypericum perforatum* and *Sambucus nigra* fruit extracts combined with colloidal silver against Gram-negative and Gram-positive microorganisms, one of the most common causes of infection difficult to treat in humans and in animals.

Materials and Methods

Plant extracts: The antimicrobial effect of *Pelargonium sidoides* DC., *Hypericum perforatum* L. and *Sambucus nigra* L. extracts in colloidal silver (AgNPs) at a concentration of 30 ppm was tested.

Preparation of the plant combination in AgNPs: The following were added to 80 ml of 30 ppm colloidal silver: 2 g of *Pelargonium sidoides* DC extract (10 capsules of 200 mg); 2 g of *Sambucus nigra* L. (5 ml of concentrated sugar syrup); 20 ml of aqueous *Hypericum perforatum* L. extract—0.4 g (1 g of dried flowers boiled in 50 ml of water for 3 minutes and soaked for 30 minutes.

Control. The broad spectrum antibiotic thiamphenicol (Nikovet Sofia) was used as positive control, to which the tested microorganisms showed no resistance.

Microorganisms. Pure cultures of 7 pathogenic strains were tested: *Esherichia coli* ATCC-8739 (NBIMCC 3397), *Salmonella enterica* subsp. *enterica* ATCC 1304 (NBIMCC 8691), *Staphylococcus aureus* subsp. *aureus* ATCC-6538 (NBIMCC 3359), *Clostridium perfringens* ATCC 13124 (NBIMCC 8615) and *Candida albicans* ATCC 10231 (NBIMCC 74). The other two (*Pseudomonas aeruginosa* and *Streptococcus pyogenes*) were isolated from inflammatory skin secretions in dogs in the microbiology laboratory of the university clinic of the Faculty of Veterinary Medicine of the University of Forestry of Sofia.

Nutrient media. Mueller Hinton agar and broth (BUL BIO NCIPD-Sofia), Columbia blood agar (Biolab Zrt. H-1141, Budapest Ov. Utra 43), as well as selective media, were used: Endo agar (Antisel-Sharlau Chemie S A, Spain) for *E. coli* and *S. enterica*, Cetrimide agar (Biolab Zrt. H-1141, Budapest Ov. Utr.) for *P. aeruginosa*, Perfringens TSC agar (MkB Test as, Slovak Republic), as well as Zeissler agar (BUL BIO NCIPD-Sofia) for *C. perfringens* and Sabouraud dextrose agar with chloramphenicol (Antisel-Sharlau Chemie S A, Spain) for *C. albicans.*

The microorganisms were grown at 35-37° C. for 18-24 and 72 hours in an anaerobic medium for *C. perfringens* and in aerobic conditions for the other microbial species. The Anaerob Pack system with —H2+CO2 palladium catalyst (BUL BIO NCIPD-Sofia) in a jar was used to create anaerobic conditions. The Indic Strip indicator (BUL BIO NCIPD-Sofia) was used to prove the creation of anaerobiosis.

The preliminary substance studies were performed using the standard agar diffusion method of Bauer et al. (1966) and according to the National Committee for Clinical Laboratory Standards (NCCLS) M2-A3 (1997, 1999). Test microorganism suspensions were inoculated in the exponential growth phase at a dose of $2 \cdot 10^6$ cells/ml in a volume of 0.1 ml in Petri dishes having a diameter of 9 cm on Zeissler agar for *C. perfringens* and Mueller-Hinton agar for the other microorganisms, with a pH of 7.2-7.4 and a layer thickness of 4 mm. 0.1 ml of the plant extracts in colloidal silver and the control antibiotic were applied in agar in wells having a diameter of 9 mm. The plant extract combination contained 2 mg of *P. sidoides,* 2 mg of *S. nigra,* 0.4 mg of *H. perforatum* and 24 ppm of AgNPs in 0.1 ml, and thiamphenicol 30 µg in 0.1 ml (according to requirements). Following a 3-4 hour incubation period at room temperature for diffusion, the cultures were incubated at 35-37° C. for 18-24 and 72 hours. The results were read by measuring the diameters of the inhibitory zones in millimetres, including the well diameter to the nearest mm, using a transparent ruler outside the plate base. According to the three stages of the Bauer-Kirby System, an inhibitory effect of the plant extracts with AgNP was observed in zones>12 mm, and thiamphenicol—at >17 mm. The susceptibility of the tested microorganisms was determined like for non-antibiotic preparations such as sulfamides, namely: resistant (R)—in zones with a diameter<12 mm, moderately—intermediate (I)—susceptible in zones between 13 and 16 mm and susceptible (S) at >17 mm. For thiamphenicol, the corresponding limits were as follows: R<12 mm, I—13-17 mm and S—>18 mm (NCCLS, 1997, 1999).

The minimum inhibitory concentrations (MIC) were determined by the two-fold serial dilution method in Zeissler agar for *C. perfringens* and Mueller-Hinton agar for the other microorganisms, as described by Ericsson and Sherris (1971) and NCCLS (1999). Bacterial suspensions were applied to a dose of $10^6$ cells/ml. The tested plant extract combination, comprising *P. sidoides, S. nigra* and *H. perforatum*, as well as the control antibiotic, were administered at different doubly growing final concentrations per ml of agar. After incubating at 35-37° C. for 18-24 hours, the number of developed colonies was determined. The MIC50 were calculated mathematically based on the number of inhibited colonies on the agar with the respective dilution of the tested compound compared to the colonies on media with controls without any plant extract or antibiotic. The growth inhibition range (D) was determined as the concentration without visible growth.

Determination of the antimicrobial action time of the plant extract combination in the AgNP. Each milliliter of combination contained 20 mg of *P. sidoides,* 20 mg of *S. nigra* and 4 mg of *H. perforatum* in the AgNPs 30 ppm.

A suspension of each microbial strain tested at a concentration of $10^5$ cells/ml in a volume of 1 ml was added to 9 ml of the plant extract combination in AgNPs, achieving a final concentration of $10^4$ cells/ml.

A suspension of each microbial strain tested at a concentration of $10^7$ cells/ml in a volume of 1 ml was added to 9 ml of the plant extract combination in the AgNP, achieving a final concentration of $10^6$ cells/ml.

The following controls were applied: sterile distilled water (without plant extracts and AgNPs) with the same content of each studied microbial strain, as well as a plant extract and AgNPs of 30 ppm, without microorganisms.

After homogenization for 1 min on a Vortex apparatus (Heidolph-Labimex, Bulgaria) and different time intervals for the exposure of microorganisms to the plant extracts in the AgNPs (1 min, 5 min, 15 min, 30 min, 60 min, 120 min, 2 h and 24 h), cultures were made from each sample on Zeissler agar for *C. perfringens* and on Mueller-Hinton agar for the other microorganisms, which were grown at 37° C. for 24-48 h in aerobic and anaerobic conditions. Following culture, the growth of the tested bacteria was reported and the number of developed colonies was determined.

All experiments were performed three times.

The findings were statistically processed using Student's and Fisher's standard method.

Findings

In the studies conducted using the disk diffusion test, an excellent inhibitory effect of the tested plant combination of *P. sidoides, S. nigra* and *H. perforatum* in the AgNPs 30 ppm (inhibitory zone diameters between 18.3+3.3 and 28.7+3.1 mm) was reported in all the tested microorganisms. The summary results are shown in table 1.

The studied Gram-negative bacteria showed greater susceptibility compared with the Gram-positive microorganisms (P>0.05, Student's t criterion). The lowest susceptibility using this approach was reported in *C. perfringens* and *S. aureus*, and the greatest—in *E. coli* and *P. aeruginosa*. All tested microorganisms showed high susceptibility to thiamphenicol used as positive control, even the tested *C. albicans* strain. However, the differences in diameter of the inhibitory zones of the studied microorganisms between the antibiotic and the tested combination with colloidal silver were not statistically significant (P>0.05, Student's t criterion).

TABLE 1

Antimicrobial effect of the tested plant extracts of
*P. sidoides, S. nigra* and *H. perforatum* with
AgNPs 30 ppm against Gram-positive and Gram-negative
microorganisms using the agar diffusion test method

| | Inhibitory zones in mm | |
| --- | --- | --- |
| Microorganisms | Combination | Thiamphenicol |
| *E. coli* | 28.7 ± 3.1 | 36.0 ± 0.8 |
| *S. enterica* | 24.0 ± 5.8 | 35.3 ± 0.8 |
| *P. aeruginosa* | 25.3 ± 4.2 | 34.8 ± 0.8 |
| *S. aureus* | 20.7 ± 4.1 | 25.7 ± 3.3 |
| *S. pyogenes* | 23.3 ± 6.7 | 26.0 ± 4.5 |
| *C. perfringens* | 18.3 ± 3.3 | 21.3 ± 0.5 |
| *C. albicans* | 21.7 ± 4.2 | 28.7 ± 3.7 |
| Total Gram-negative | 25.9 ± 2.0 | 35.4 ± 0.5 |
| Total Gram-positive bacteria | 20.8 ± 2.0 | 24.3 ± 2.1 |
| Total bacteria | 23.3 ± 3.3 | 29.9 ± 5.7 |
| Total (all microorganisms) | 23.1 ± 3.1 | 29.7 ± 5.3 |

However, when determining the minimum inhibitory concentrations of the tested plant extracts compared to the strains used, the differences in susceptibility between the Gram-positive and Gram-negative microorganisms were better expressed and were significant (P>0.001, Student's t criterion). The results are shown in table 2. The growth of the Gram-negative bacteria was completely inhibited by much lower plant extract concentrations (the MIC50 of *P. sidoides, S. nigra* and *H. perforatum* were respectively 5.0+0.0, 5.0+0.0 and 50.0+0.0) compared to the Gram-positive bacteria and *C. albicans* (the MIC50 of *P. sidoides, S. nigra* and *H. perforatum* were 10.0+0.0, 10.0+0.0 and 100.0+0.0 respectively). With this method, the susceptibility of the fungus *C. albicans* to the tested plant extract combination did not differ from that of the Gram-positive bacteria.

TABLE 2

Minimum inhibitory concentrations of a combination of the tested plant extracts
in water against Gram-positive and Gram-negative microorganisms.

| | Minimum inhibitory concentrations | | | | | | | |
| --- | --- | --- | --- | --- | --- | --- | --- | --- |
| | $MIC_{50}$ (mg/ml) | | | D (mg/ml) | | | Th (μg/ml) | |
| Microorganisms | P. | S. | H. | P. | S. | H. | $MIC_{50}$ | D |
| *Esherichia coli* | 5 | 5 | 50 | 10 | 10 | 100 | 8 | 64 |
| *Salmonella enterica* | 5 | 5 | 50 | 10 | 10 | 100 | 16 | 64 |
| *Pseudominas aeruginosa* | 5 | 5 | 50 | 10 | 10 | 100 | 8 | 64 |
| *Staphylococcus aureus* | 10 | 10 | 100 | 20 | 20 | 200 | 16 | 64 |
| *Streptococcus pyogenes* | 10 | 10 | 100 | 20 | 20 | 200 | 32 | 128 |
| *Clostridium perfringens* | 10 | 10 | 100 | 20 | 20 | 200 | 4 | 16 |
| *Candida albicans* | 10 | 10 | 100 | 20 | 20 | 200 | 32 | 128 |
| Total Gram-negative | 5.0 ± 0.0 | 5.0 ± 0.0 | 50.0 ± 0.0 | 10.0 ± 0.0 | 10.0 ± 0.0 | 100.0 ± 0.0 | 10.67 ± 3.77 | 64.00 ± 0.00 |
| Total Gram-positive | 10.0 ± 0.0 | 10.0 ± 0.0 | 100.0 ± 0.0 | 20.0 ± 0.0 | 20.0 ± 0.0 | 200.0 ± 0.0 | 21.00 ± 11.79 | 42.00 ± 2.36 |

TABLE 2-continued

Minimum inhibitory concentrations of a combination of the tested plant extracts
in water against Gram-positive and Gram-negative microorganisms.

| | Minimum inhibitory concentrations | | | | | | | |
| | MIC$_{50}$ (mg/ml) | | | D (mg/ml) | | | Th (µg/ml) | |
| Microorganisms | P. | S. | H. | P. | S. | H. | MIC$_{50}$ | D |
|---|---|---|---|---|---|---|---|---|
| Total bacteria | 7.5 ± 2.5 | 7.5 ± 2.5 | 66.7 ± 37.3 | 15.0 ± 5.0 | 15.0 ± 5.0 | 150.0 ± 50.0 | 14.0 ± 9.2 | 66.7 ± 32.6 |
| Total (all microorganisms) | 7.9 ± 2.7 | 7.9 ± 2.7 | 78.6 ± 24.7 | 15.7 ± 4.9 | 15.7 ± 4.9 | 157.1 ± 49.5 | 16.57 ± 10.57 | 84.00 ± 47.16 |

MIC50 -50% growth inhibition; D - complete growth inhibition range; P.- P. sidoides; S. - S. nigra; H. - H. perforatum; Th - Thiamphenicol The results of the studies conducted to determine the susceptibility of the tested Gram-positive and Gram-negative microorganisms to the plant extract combination in the AgNP, tested at a final concentration of 10$^6$ cells/ml using the suspension method, are shown in table 3.

The data shows that the plant combination in the AgNPs inactivated all the tested microbial strains within 24 h. All the studied Gram-negative bacteria strains showed a particularly high susceptibility. They died within a period of 1 to 15 minutes. Among the Gram-positive microorganisms, the C. perfringens cells survived for the shortest period of time—up to 60 min, as well as those of S. pyogenes. In the others (S. aureus and C. albicans), individual cells remained viable for more than 2 hours.

TABLE 3

Minimum inhibitory concentrations of a combination of the tested plant extracts
in water against Gram-positive and Gram-negative microorganisms

| | Strain growth (percentage of the number of colonies compared to the unprocessed controls) after different exposure intervals | | | | | | |
| Microorganisms | 1 min | 5 min | 15 min | 30 min | 60 min | 120 min | 24 h |
|---|---|---|---|---|---|---|---|
| E. coli | 0 | 0 | 0 | 0 | 0 | 0 | 0 |
| S. enterica | 10 | 5 | 0 | 0 | 0 | 0 | 0 |
| P. aeruginosa | 10 | 5 | 0 | 0 | 0 | 0 | 0 |
| S. aureus | 60 | 50 | 140 | 25 | 20 | 10 | 0 |
| S. pyogenes | 30 | 20 | 15 | 10 | 5 | 0 | 0 |
| C. perfringens | 25 | 15 | 10 | 5 | 0 | 0 | 0 |
| C. albicans | 60 | 50 | 25 | 20 | 20 | 5 | 0 |
| Unprocessed controls | 100 | 100 | 100 | 100 | 100 | 100 | 100 |

TABLE 4

Antimicrobial effect of the tested plant extracts of P. sidoides, S. nigra
and H. perforatum with AgNPs 30 ppm against Gram-positive and Gram-negative
microorganism suspensions with a concentration of 10$^4$ cells/ml

| | Strain growth (percentage of the number of colonies compared to the unprocessed controls) after different exposure intervals | | | | | | |
| Microorganisms | 1 min | 5 min | 15 min | 30 min | 60 min | 120 min | 24 h |
|---|---|---|---|---|---|---|---|
| E. coli | 0 | 0 | 0 | 0 | 0 | 0 | 0 |
| S. enterica | 0 | 0 | 0 | 0 | 0 | 0 | 0 |
| P. aeruginosa | 0 | 0 | 0 | 0 | 0 | 0 | 0 |
| S. aureus | 40 | 30 | 25 | 20 | 10 | 5 | 0 |
| S. pyogenes | 25 | 20 | 10 | 5 | 0 | 0 | 0 |
| C. perfringens | 20 | 10 | 5 | 0 | 0 | 0 | 0 |
| C. albicans | 45 | 30 | 15 | 10 | 5 | 0 | 0 |
| Unprocessed controls | 100 | 100 | 100 | 100 | 100 | 100 | 100 |

A significantly quicker bactericidal effect was shown by the tested combination of *P. sidoides, S. nigra* and *H. perforatum* in colloidal silver compared to the studied Gram-positive and Gram-negative microorganisms, when applied at a final concentration of $10^4$ cells/ml. The summary data is shown in table 4.

The results showed that when suspended with this lower concentration, the Gram-negative bacteria died within 1 minute in the presence of the plant combination. Among the Gram-positive species, *C. perfringens* (up to 15 min) and *S. pyogenes* (up to 30 min) survived for the shortest period of time. The individual cells of *C. albicans* and *S. aureus* remained viable for 1 and 2 h, respectively.

Current studies of the antimicrobial activity of the combination of *P. sidoides, S. nigra* and *H. perforatum* in the AgNPs 30 ppm showed a significant susceptibility of the studied microorganisms of different groups, which was significantly high in the Gram-negative bacteria, including the *P. aeruginosa*—species, which rapidly developed a resistance to chemical factors. It is also important to note that the significantly high susceptibility of the strict anaerobe *C. perfringens*, established by all the used research methods.

These results show a successful application of this combination as antiseptic, as well as for the topical treatment of infections involving these bacteria. The antifungal effect of the combination is also significant.

Conclusions

1. The combination of *P. sidoides, S. nigra* and *H. perforatum* in AgNPs 30 ppm showed an excellent inhibitory effect against all tested microorganisms (inhibitory zone diameters between 18.3+3.3 and 28.7+3.1 mm) with the agar diffusion method. The Gram-negative bacteria, in particular *E. coli* and *P. aeruginosa*, showed a greater susceptibility, and *C. perfringens* and *S. aureus* had a lower susceptibility.
2. The tested microorganisms were eliminated by very low concentrations of plant extracts applied in combination. The MIC50 of *P. sidoides, S. nigra* and *H. perforatum* were respectively 5.0+0.0, 5.0+0.0 and 50.0+0.0 for the Gram-negative bacteria. For the Gram-positive bacteria and *C. albicans*, the MIC50 of *P. sidoides, S. nigra* and *H. perforatum* were respectively 10.0+0.0, 10.0+0.0 and 100.0+0.0.
3. In the studies on suspensions, the plant combination in the AgNPs proved to be inactive for all the tested bacterial strains within 24 hours when examined at a final concentration of $10^6$ cells/ml. The Gram-negative bacterial strains showed a significantly high susceptibility (dead within a period of 1 to 15 minutes). Among the Gram-positive microorganisms, the *C. perfringens* cells survived for the shortest period of time—up to 60 minutes—as well as those of *S. pyogenes*. The individual cells of *S. aureus* and *C. albicans* remained viable for more than 2 hours.
4. A significantly quicker bactericidal effect was shown by the tested combination of *P. sidoides, S. nigra* and *H. perforatum* in colloidal silver compared to the studied microorganisms, when applied to a final concentration of $10^4$ cells/ml. The gram-negative bacteria died within 1 minute. Among the Gram-positive species, *C. perfringens* (up to 15 min) and *S. pyogenes* (up to 30 min) survived for the shortest period of time. The individual cells of *C. albicans* and *S. aureus* remained viable for 1 and 2 h, respectively.

5. The results revealed the efficacy of this plant combination with AgNPs for the antiseptic effect, as well as for the local treatment of bacterial and fungal infections.

Example 7: Complementary Study Protocol of the In Vitro Antimicrobial Activity for the Combination of *Pelargonium sidoides, Sambucus nigra* and *Hypericum Perforatum* Extracts with Colloidal Silver The aim of this work was to carry out studies to assess the in vitro antimicrobial activity of extracts of the following combinations African geranium (*Pelargonium sidoides* DC.) & black elderberry (*Sambucus nigra* L.), Saint John's Wort (*Hypericum perforatum* L.) & black elderberry (*Sambucus nigra* L.) and African geranium (*Pelargonium sidoides* DC.) & Saint John's Wort (*Hypericum perforatum* L.) as colloidal nano-silver and as aqueous extracts.) and African geranium (*Pelargonium sidoides* DC.) & Saint John's Wort (*Hypericum perforatum* L.) as colloidal nano-silver and as aqueous extracts against Gram-negative and Gram-positive microorganisms, one of the most common causes of infection that is difficult to treat in humans and animals.

Materials and Methods

Plant extracts. The antimicrobial effect of the aqueous African geranium (*Pelargonium sidoides* DC.), Saint John's Wort (*Hypericum perforatum* L.) and black elderberry (*Sambucus nigra* L.) extracts was tested. The same extracts were examined with nanoparticles of colloidal silver (AgNPs) at a concentration of 30 ppm.

Control. The broad spectrum antibiotic thiamphenicol (Nikovet Sofia) was used as positive control, to which the tested microorganisms showed no resistance.

Microorganisms. Pure cultures of 7 pathogenic strains were tested. Five of them are references from Bulgaria's National Bank for Industrial Microorganisms and Cell Cultures (NBIMCC): *Esherichia coli* ATCC-8739 (NBIMCC 3397), *Salmonella enterica* subsp. *enterica* ATCC 1304 (NBIMCC 8691), *Staphylococcus aureus* subsp. *aureus* ATCC-6538 (NBIMCC 3359), *Clostridium perfringens* ATCC 13124 (NBIMCC 8615) and *Candida albicans* ATCC 10231 (NBIMCC 74). The other two (*Pseudomonas aeruginosa* and *Streptococcus pyogenes*) were isolated from dog inflammatory skin secretions in the microbiology laboratory of the university clinic of the University of Forestry, Faculty of Veterinary Medicine of Sofia.

Nutrient media. Mueller Hinton agar and broth (BUL BIO NCIPD-Sofia), Columbia blood agar (Biolab Zrt. H-1141, Budapest Ov. Utra 43), as well as selective media, were used: Endo agar (Antisel Sharlau Chemie S A, Spain) for *E. coli* and *S. enterica*, Cetrimide agar (Biolab Zrt. H-1141, Budapest Ov. Utr.) for *P. aeruginosa*, TSC *Perfringens agar* (MkB Test as, Slovakia), as well as Zeissler agar (BUL BIO NCIPD-Sofia) for *C. perfringens* and Sabouraud dextrose agar with chloramphenicol (Antisel Sharlau Chemie S A, Spain) for *C. albicans*.

The microorganisms were grown at 35-37° C. for 18-24 and 72 hours in an anaerobic environment for *C. perfringens* and in aerobic conditions for the other microbial species. The Anaerob Pack system with —H2+CO2 palladium catalyst (BUL BIO NCIPD-Sofia) in a jar was used to create anaerobic conditions. The Strip indicator (BUL BIO NCIPD-Sofia) was used to prove the creation of anaerobiosis.

The preliminary substance studies were performed using the standard method of diffusion on Bauer et al. agar (1966) and according to the National Committee for Clinical Laboratory Standards (NCCLS) M2-A3 (1997, 1999). Microorganism suspensions to be tested were inoculated in the exponential growth phase at a dose of $2.10^6$ cells/ml in a volume of 0.1 ml in Petri dishes with a diameter of 9 cm on Zeissler agar for *C. perfringens* and Mueller-Hinton agar for the other microorganisms, with a pH of 7.2-7.4 and a layer thickness of 4 mm. 0.1 ml of plant extracts in colloidal silver and in water, as well as the control antibiotic, were applied in agar in 9 mm wells. The plant extracts, alone and in combination, respectively contained 2 mg of *P. sidoides*, 2 mg of *S. nigra*, 0.4 mg of *H. perforatum* and 24 ppm of AgNPs or water in 0.1 ml, and thiamphenicol—30 μg in 0.1 ml (as necessary). Following a 3-4 hour incubation period at room temperature for diffusion, the cultures were incubated at 35-37° C. for 18-24 and 72 hours. The results were read by measuring the diameters of the inhibitory zones in millimetres, including the well diameter to the nearest mm, using a transparent ruler outside the plate base. According to the three-stage Bauer-Kirby system, an inhibitory effect of the plant extracts with or without AgNPs was observed in zones>12 mm, and thiamphenicol at >17 mm. The susceptibility of the tested microorganisms was determined like for the non-antibiotic preparations such as sulfamides, namely: resistant (R) in zones with a diameter<12 mm, moderately susceptible intermediate (I) in zones between 13 and 16 mm and susceptible (S) at >17 mm. For thiamphenicol, the corresponding limits were as follows: R<12 mm, I—13-17 mm and S—>18 mm (NCCLS, 1997, 1999).

The minimum inhibitory concentrations (MIC) were determined using two-fold serial dilutions in Zeissler agar for *C. perfringens* and Mueller-Hinton agar for the other microorganisms, described by Ericsson and Sherris (1971) and NCCLS (1999). Bacterial suspensions were applied at a dose of $10^6$ cells/ml. The tested plant extracts of *P. sidoides, S. nigra* and *H. perforatum*, alone or in combination, in water or with AgNPs, as well as the control antibiotic, were administered at different doubly growing final concentrations per ml of agar. After incubating at 35-37° C. for 18-24 hours, the number of developed colonies was determined. The MIC50 were calculated mathematically based on the number of inhibited colonies on the agar with the respective dilution of the tested compound compared to the colonies on the media with controls without any plant extracts or antibiotic. The growth inhibition interval (D) was determined as the concentration without visible growth.

Determination of the antimicrobial action time of the aqueous plant extracts and those with colloidal nano silver. Each milliliter of extract contained 20 mg of *P. sidoides*, 20 mg of *S. nigra* and 4 mg of *H. perforatum*, respectively, and when the AgNPs were added, their final concentration was 24 ppm.

A suspension of each tested microbial strain with a concentration of $10^5$ cells/ml in a volume of 1 ml was added to 9 ml of the plant extract combination in water, as well as to 9 ml of aqueous extracts of each of these plants separately, where the final concentration became $10^4$ cells/ml. The same procedure was applied with the extracts containing AgNPs alone and separately.

A suspension of each microbial strain tested at a concentration of $10^7$ cells/ml in a volume of 1 ml was added to 9 ml of the plant extract combination, as well as to 9 ml of extracts of each of these plant extracts separately, where the final concentration of $10^6$ cells/ml was achieved. The same procedure was applied with the extracts containing AgNPs alone and separately.

The following controls were applied: sterile distilled water (without plant extracts and AgNPs) with the same content of each studied microbial strain, as well as a plant extract and AgNPs 30 ppm, without microorganisms.

After homogenization for 1 min on a Vortex apparatus (Heidolph-Labimex, Bulgaria) and different time intervals for the exposure of microorganisms to the tested plant extracts (1 min, 5 min, 15 min, 30 min, 60 min, 120 min, 2 h and 24 h), cultures were made from each sample on Zeissler agar for *C. perfringens* and on Mueller-Hinton agar for the other microorganisms, which were grown at 37° C. for 24-48 h in aerobic and anaerobic conditions. Following culture, the growth of the tested bacteria was reported and the number of developed colonies was determined.

All experiments were performed three times.

The findings were statistically processed using Student's and Fisher's standard method.

Findings

In the studies performed using the agar disk diffusion method, an excellent inhibitory effect of the extracts of all the tested plants examined with AgNPs (inhibitory zone diameter between 16.0+0.6 and 24.3+1.3 mm) and the combination between them was reported (inhibitory zones between 18.3+3.3 and 28.7+3.1 mm) in all tested microorganisms. The summary data is shown in table 5. The effect of the combination of extracts of the three plants with AgNPs was greater than that with extracts with AgNPs applied separately. The differences in the mean inhibitory zone diameters (without microbial growth) between the individual plant extracts and the combination between them were not significant (P>0.05).

TABLE 5

Antimicrobial effect of the tested plant extracts (*P. sidoides* &. *S. nigra*; *S. nigra* & *H. perforatum*; *H. perforatum* & *P. sidoides*) in AgNPs against Gram-positive and Gram-negative microorganisms using the agar-gel diffusion method.

| Microorganism | Inhibitory zones in mm | | | | |
| --- | --- | --- | --- | --- | --- |
| | Combination | *P. sidoides*& *S. nigra* | *S. nigra*& *H. perforatum* | *H. perforatum*& *P. sidoides* | Thiamphenicol |
| *E. coli* | 28.7 ± 3.1 | 25.1 ± 1.3 | 25.3 ± 1.1 | 24.2 ± 0.9 | 36.0 ± 0.8 |
| *S. enterica* | 24.0 ± 5.8 | 23.2 ± 1.2 | 23.1 ± 1.0 | 22.9 ± 0.7 | 35.3 ± 0.8 |
| *P. aeruginosa* | 25.3 ± 4.2 | 24.1 ± 1.2 | 23.7 ± 1.5 | 23.7 ± 1.0 | 34.8 ± 0.8 |
| *S. aureus* | 20.7 ± 4.1 | 18.5 ± 1.1 | 19.1 ± 0.9 | 17.2 ± 0.6 | 25.7 ± 3.3 |
| *S. pyogenes* | 23.3 ± 6.7 | 21.7 ± 0.5 | 20.8 ± 0.6 | 21.8 ± 0.9 | 26.0 ± 4.5 |
| *C. perfringens* | 18.3 ± 3.3 | 17.2 ± 0.8 | 17.3 ± 0.8 | 16.9 ± 0.5 | 21.3 ± 0.5 |

TABLE 5-continued

Antimicrobial effect of the tested plant extracts (*P. sidoides &. S. nigra*;
*S. nigra & H. perforatum*; *H. perforatum & P. sidoides*) in AgNPs against
Gram-positive and Gram-negative microorganisms using the agar-gel diffusion method.

| | | Inhibitory zones in mm | | | |
| Microorganism | Combination | *P. sidoides& S. nigra* | *S. nigra& H. perforatum* | *H. perforatum& P. sidoides* | Thiamphenicol |
| --- | --- | --- | --- | --- | --- |
| *C. albicans* | 21.7 ± 4.2 | 19.1 ± 0.8 | 18.8 ± 0.5 | 18.5 ± 0.5 | 28.7 ± 3.7 |
| Total Gram-negative | −25.9 ± 2.0 | 24.3 ± 1.3 | 22.8 ± 1.1 | 23.1 ± 0.7 | 35.4 ± 0.5 |
| Total Gram-positive | −20.8 ± 2.0 | 19.1 ± 1.9 | 18.7 ± 1.2 | 18.0 ± 2.1 | 24.3 ± 2.1 |
| Total bacteria | 23.3 ± 3.3 | 21.4 ± 2.8 | 20.7 ± 2.3 | 21.7 ± 2.6 | 29.9 ± 5.7 |
| Total (all microorganisms) | 23.1 ± 3.1 | 21.8 ± 2.6 | 22.2 ± 2.3 | 21.7 ± 2.3 | 29.7 ± 5.3 |

The aqueous extracts of all the tested plants, as well as the combination between them (inhibitory zone diameters between 16.0+0.6 and 26.0+3.7 mm) also showed a high inhibitory effect on all tested microorganisms in the studies performed using the disk diffusion method. The results are shown in table 6. The effect of the combination between the extracts of the three plants was greater than that with extracts applied separately. The differences in the mean diameters of the non-growth zones between the individual plant extracts and the combination between them were not significant (P>0.05).

TABLE 6

Antimicrobial effect of the tested plant extracts (*P. sidoides &. S. nigra*;
*S. nigra & H. perforatum*; *H. perforatum & P. sidoides*) in water tested against
Gram-positive and Gram-negative microorganisms using the agar-gel diffusion method

| | | Inhibitory zones in mm | | | |
| Microorganisms | Combination | *P. sidoides& S. nigra* | *S. nigra& H. perforatum* | *H. perforatum &P. sidoides* | Thiamphenicol |
| --- | --- | --- | --- | --- | --- |
| *E. coli* | 26.0 ± 3.7 | 24.5 ± 1.3 | 23.7 ± 1.1 | 22.5 ± 0.9 | 36.0 ± 0.8 |
| *S. enterica* | 23.3 ± 1.7 | 21.4 ± 1.4 | 22.0 ± 2.0 | 21.5 ± 1.6 | 35.3 ± 0.8 |
| *P. aeruginosa* | 24.0 ± 2.4 | 22.5 ± 1.4 | 22.6 ± 2.5 | 22.3 ± 1.0 | 34.8 ± 0.8 |
| *S. aureus* | 18.7 ± 2.8 | 17.1 ± 0.8 | 17.9 ± 0.8 | 17.1 ± 0.8 | 25.7 ± 3.3 |
| *S. pyogenes* | 22.0 ± 4.8 | 21.7 ± 2.6 | 19.5 ± 0.7 | 21.6 ± 0.9 | 26.0 ± 4.5 |
| *C. perfringens* | 17.9 ± 3.5 | 17.4 ± 0.8 | 17.4 ± 0.8 | 17.4 ± 1.3 | 21.3 ± 0.5 |
| *C. albicans* | 20.7 ± 4.8 | 18.4 ± 1.1 | 17.3 ± 0.6 | 18.8 ± 1.6 | 28.7 ± 3.7 |
| Total Gram-negative | 24.4 ± 1.1 | 22.7 ± 0.9 | 22.6 ± 0.7 | 21.2 ± 0.5 | 35.4 ± 0.5 |
| Total Gram-positive | 19.5 ± 1.8 | 19.1 ± 3.1 | 18.7 ± 0.6 | 17.7 ± 2.1 | 24.3 ± 2.1 |
| Total bacteria | 22.0 ± 2.9 | 21.2 ± 2.6 | 21.3 ± 2.0 | 18.5 ± 2.1 | 29.9 ± 5.7 |
| Total (all microorganisms) | 21.8 ± 2.7 | 21.2 ± 2.8 | 20.2 ± 2.2 | 19.8 ± 1.9 | 29.7 ± 5.3 |

A slightly greater susceptibility to all the studied plants, as well as to their combination, was shown by the Gram-negative bacteria tested compared to the Gram-positive microorganisms (P>0.05). The greatest susceptibility using this method was found in *E. coli* and *P. aeruginosa*. Fungus *C. albicans* also showed a susceptibility to all the studied plants. All tested microorganisms showed high susceptibility to thiamphenicol, used as positive control. The differences in the diameters of the inhibitory zones of all the strains in the antibiotic and the studied extracts were statistically significant (P<0.05).

The results obtained during the determination of the minimum inhibitory concentrations (MIC) are shown in table 7. They correspond to those of the agar-gel diffusion method. The studied extracts of the three plants showed a significant antimicrobial activity. The effect of *P. sidoides* and *S. nigra* was similar. Their MIC50 for Gram-negative bacteria was low—10 mg/ml, and 20 mg/ml for Gram-positive microorganisms. The growth of the studied microbial strains was inhibited by greater concentrations of *H. perforatum* 50 mg/ml for the Gram-negative strains and 100 mg/ml for the Gram-positive strains.

When applied in combination, these extracts showed a synergetic activity. The same antimicrobial effect was obtained at concentrations that were twice as low. The differences in MIC50 of *P. sidoides* and *S. nigra*, tested alone and in combination, were significant (P<0.01) in favour of the combination.

TABLE 7

Minimum inhibitory concentrations of the tested plant extracts (*P.*
*Sidoides* & *S.nigra*; *S. nigra* & *H.perforatum*; *H. perforatum* & *P.sidoides*) in water
against Gram-positive and Gram-negative microorganisms.

| | Minimum inhibitory concentrations in mg/ml | | | | | |
| | *P. sidoides*& *S.nigra* | | *S. nigra*& *H.perforatum* | | *H. perforatum* &*P.sidoides* | |
| Microorganisms | MIC$_{50}$ | D | MIC$_{50}$ | D | MIC$_{50}$ | D |
|---|---|---|---|---|---|---|
| *Esherichia coli* | 10 | 100 | 10 | 50 | 50 | 100 |
| *Salmonella enterica* | 10 | 100 | 10 | 50 | 50 | 100 |
| *Pseudominas aeruginosa* | 10 | 100 | 10 | 50 | 50 | 100 |
| *Staphylococcus aureus* | 15 | 100 | 15 | 100 | 100 | 200 |
| *Streptococcus pyogenes* | 15 | 100 | 15 | 100 | 100 | 200 |
| *Clostridium perfringens* | 15 | 100 | 15 | 100 | 100 | 200 |
| *Candida albicans* | 15 | 100 | 15 | 100 | 100 | 200 |
| Total Gram-negative | 10.0 ± 0.0 | 100.0 ± 0. | 10.0 ± 0.0 | 50.0 ± 0.0 | 50.0 ± 0.0 | 100.0 ± 0.0 |
| Total Gram-positive | 15.0 ± 0.0 | 100.0 ± 0.0 | 20.0 ± 0.0 | 100.0 ± 0.0 | 100.0 ± 0.0 | 200.0 ± 0.0 |
| Total bacteria | 10.0 ± 3.0 | 100.0 ± 0.0 | 15.0 ± 5.0 | 66.7 ± 37.3 | 66.7 ± 37.3 | 150.0 ± 50.0 |
| Total (all microorganisms) | 11.5 ± 3.8 | 100.0 ± 0.0 | 15.7 ± 4.9 | 78.6 ± 24.7 | 78.6 ± 24.7 | 157.1 ± 49.5 |

MIC$_{50}$-50% growth inhibition;
D-total growth inhibition range

The data of the studies using the suspension method showed that the tested aqueous plant extracts, applied in combination, had a significant antimicrobial activity (Table 8). When the plant combination contained AgNPs, the *aureus*—for more than two hours. In the silver-free aqueous extracts, the reduction of tested microorganisms of all groups was slower than when the plant combination contained colloidal nanosilver.

TABLE 8

Antimicrobial effect of the tested plant extracts (*P. sidoides* &
*S.nigra*) (*S. nigra* & *H.perforatum*) (*H. perforatum* & *P.sidoides*) in combination with the
AgNPs and in water against Gram-positive and Gram-negative microorganisms in
suspensions with a concentration of $10^6$ cells/ml.

| | Microorganisms Strain growth (percentage of the number of colonies compared to the unprocessed controls) after different exposure intervals. | | | | | | | | | | | | | |
| | 1 min | | 5 min | | 15 min | | 30 min | | 60 min | | 120 min | | 24 h | |
| | Ag | W | Ag | W | Ag | W | Ag | W | Ag | W | Ag | W | Ag | W |
|---|---|---|---|---|---|---|---|---|---|---|---|---|---|---|
| *E. coli* | 0 | 5 | 0 | 0 | 0 | 0 | 0 | 0 | 0 | 0 | 0 | 0 | 0 | 0 |
| *S. enterica* | 10 | 15 | 5 | 5 | 0 | 5 | 0 | 0 | 0 | 0 | 0 | 0 | 0 | 0 |
| *P. aeruginosa* | 10 | 15 | 5 | 5 | 0 | 0 | 0 | 0 | 0 | 0 | 0 | 0 | 0 | 0 |
| *S. aureus* | 60 | 70 | 45 | 50 | 35 | 40 | 20 | 30 | 10 | 20 | 5 | 10 | 0 | 0 |
| *S. pyogenes* | 30 | 40 | 20 | 20 | 15 | 15 | 10 | 10 | 5 | 5 | 0 | 0 | 0 | 0 |
| *C. perfringens* | 25 | 25 | 10 | 20 | 10 | 15 | 0 | 5 | 0 | 0 | 0 | 0 | 0 | 0 |
| *C. albicans* | 60 | 60 | 45 | 50 | 20 | 30 | 25 | 35 | 15 | 10 | 0 | 5 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

bactericidal effect was quicker than without silver. As shown by the table data, when suspended with a concentration of $10^6$ cells/ml, the studied Gram-negative bacteria died rapidly—*E. coli* for 1 min with silver and up to 5 min without silver, *P. aeruginosa* respectively for 15-30 min, and *S. enterica* within 30 min.

The plant extract combination also inactivated the Gram-positive microorganisms studied in a suspension with a concentration of $10^6$ cells/ml, but for a longer period of time—*C. perfringens* for 30 to 60 min, *S. pyogenes* for at least 1 hour, *C. albicans*—for at least two hours and *S.*

When suspended at a concentration of $10^4$ cells/ml, the tested microorganisms showed greater susceptibility to the tested plant extracts applied in combination. Their quantities decreased more rapidly under the action of the means examined. When the plant combination contained AgNPs, its bactericidal effect was quicker than without silver. The results of this research are shown in table 9. In this experimental design, the tested Gram-negative bacteria died within a much shorter period of time. In the presence of nanosilver—for 1 min, and without nanosilver—for 5 min.

TABLE 9

Antimicrobial effect of the *P. sidoides* & *S.Nigra* extract with AgNPs
and in water against the Gram-positive and Gram-negative microorganisms in
suspensions with a concentration of $10^4$ cells/ml

| | Strain growth (percentage of the number of colonies compared to the unprocessed controls) after different exposure intervals. | | | | | | | | | | | | | |
| | 1 min | | 5 min | | 15 min | | 30 min | | 60 min | | 120 min | | 24 h | |
| Microorganisms | Ag | W | Ag | W | Ag | W | Ag | W | Ag | W | Ag | W | Ag | W |
|---|---|---|---|---|---|---|---|---|---|---|---|---|---|---|
| *E. coli* | 0 | 6 | 0 | 0 | 0 | 0 | 0 | 0 | 0 | 0 | 0 | 0 | 0 | 0 |
| *S. enterica* | 0 | 4 | 0 | 0 | 0 | 0 | 0 | 0 | 0 | 0 | 0 | 0 | 0 | 0 |
| *P. aeruginosa* | 0 | 5 | 0 | 0 | 0 | 0 | 0 | 0 | 0 | 0 | 0 | 0 | 0 | 0 |
| *S. aureus* | 50 | 54 | 25 | 45 | 30 | 35 | 20 | 25 | 15 | 15 | 4 | 5 | 0 | 0 |
| *S. pyogenes* | 25 | 30 | 20 | 25 | 15 | 15 | 10 | 15 | 5 | 5 | 5 | 5 | 0 | 0 |
| *C. perfringens* | 20 | 30 | 15 | 20 | 10 | 10 | 5 | 5 | 5 | 5 | 0 | 5 | 0 | 0 |
| *C. albicans* | 50 | 60 | 35 | 40 | 20 | 20 | 10 | 15 | 5 | 10 | 0 | 5 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

The plant extract combination also inactivated the Gram-positive microorganisms studied in a suspension with a concentration of $10^4$ cells/ml, however for a longer period of time—the anaerobe *C. perfringens* for 30 minutes, and the other bacterial species and the oval fungus *C. albicans* for more than two hours. As shown in the table data, in the silver-free aqueous extracts, the reduction of the tested microorganisms of all groups was slower than when the plant combination contained colloidal nanosilver.

The results of the studies of the African geranium (*P. sidoides*) & *H. perforatum* extract in the suspension method are shown in table 10. The plant extract showed significant antimicrobial activity, which increased with the addition of colloidal nanosilver. The studied Gram-negative bacteria suspensions with a concentration of $10^6$ cells/ml died within quite a short period of time—*E. coli* and *S. enterica* up to 5 minutes with nanosilver and up to 15 minutes without silver, and *P. aeruginosa*—within 15 minutes with silver and approx. 30 minutes without nanosilver. The *P. sidoides* & *H. perforatum* extract inactivated the studied Gram-positive microorganisms, but for more than two hours.

TABLE 10

Antimicrobial effect of the *P. sidoides* & *H.perforatum* extract with
AgNPs and with water against the Gram-positive and Gram-negative microorganisms in
suspensions with a concentration of $10^6$ cells/ml.

| | Strain growth (percentage of the number of colonies compared to the unprocessed controls) after different exposure intervals. | | | | | | | | | | | | | |
| | 1 min | | 5 min | | 15 min | | 30 min | | 60 min | | 120 min | | 24 h | |
| Microorganisms | Ag | W | Ag | W | Ag | W | Ag | W | Ag | W | Ag | W | Ag | W |
|---|---|---|---|---|---|---|---|---|---|---|---|---|---|---|
| *E. coli* | 5 | 10 | 0 | 5 | 0 | 0 | 0 | 0 | 0 | 0 | 0 | 0 | 0 | 0 |
| *S. enterica* | 10 | 10 | 0 | 10 | 0 | 0 | 0 | 0 | 0 | 0 | 0 | 0 | 0 | 0 |
| *P. aeruginosa* | 10 | 12 | 5 | 8 | 0 | 5 | 0 | 5 | 0 | 0 | 0 | 0 | 0 | 0 |
| *S. aureus* | 60 | 65 | 40 | 70 | 35 | 50 | 30 | 35 | 15 | 35 | 10 | 10 | 0 | 0 |
| *S. pyogenes* | 55 | 55 | 30 | 60 | 25 | 35 | 10 | 25 | 10 | 20 | 5 | 10 | 0 | 0 |
| *C. perfringens* | 35 | 50 | 25 | 45 | 10 | 25 | 5 | 15 | 5 | 5 | 5 | 5 | 0 | 0 |
| *C. albicans* | 60 | 60 | 35 | 70 | 30 | 45 | 20 | 30 | 10 | 20 | 5 | 5 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

Table 11 shows the test results of the suspension method of the black elderberry (*S. nigra*) & *H. perforatum* extract and the *H. perforatum* & *P. sidoides* extract. All the Gram-negative bacteria tested in a suspension with a concentration of $10^6$ cells/ml died within 15 to 30 minutes, although a lot sooner when the extract contained nanosilver. These extracts also inactivated the studied Gram-positive microorganisms, however for a longer period of time—over two hours. For the extracts containing silver, the reduction of the tested microorganisms of all groups was quicker compared to the aqueous extract.

TABLE 11

Antimicrobial effect of the *S.Nigra* & *H. perforatum* extract with
AgNPs 30 ppm and with water against the Gram-positive and Gram-negative
microorganisms in suspensions with a concentration of $10^6$ cells/ml.

Strain growth (percentage of the number of colonies compared
to the unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 5 | 10 | 0 | 5 | 0 | 0 | 0 | 0 | 0 | 0 | 0 | 0 | 0 | 0 |
| *S. enterica* | 5 | 10 | 0 | 5 | 0 | 0 | 0 | 0 | 0 | 0 | 0 | 0 | 0 | 0 |
| *P. aeruginosa* | 10 | 15 | 5 | 8 | 0 | 5 | 0 | 0 | 0 | 0 | 0 | 0 | 0 | 0 |
| *S. aureus* | 55 | 60 | 55 | 70 | 40 | 45 | 35 | 40 | 25 | 30 | 10 | 15 | 0 | 0 |
| *S. pyogenes* | 40 | 50 | 40 | 60 | 30 | 50 | 30 | 30 | 10 | 20 | 10 | 10 | 0 | 0 |
| *C. perfringens* | 40 | 50 | 30 | 50 | 25 | 30 | 20 | 25 | 10 | 20 | 0 | 5 | 0 | 5 |
| *C. albicans* | 50 | 60 | 45 | 60 | 40 | 45 | 30 | 40 | 15 | 30 | 5 | 10 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs 30 ppm;
W-combination of plant extracts in water.

TABLE 12

Antimicrobial effect of the *H. perforatum* & *P. sidoides* extract with
AgNPs 30 ppm against the Gram-positive and Gram-negative microorganisms in
suspensions with a concentration of $10^4$ cells/ml Strain growth (percentage of the number of colonies compared to the
unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 10 | 20 | 5 | 10 | 0 | 0 | 0 | 0 | 0 | 0 | 0 | 0 | 0 | 0 |
| *S. enterica* | 20 | 25 | 10 | 15 | 0 | 0 | 0 | 0 | 0 | 0 | 0 | 0 | 0 | 0 |
| *P. aeruginosa* | 10 | 20 | 5 | 10 | 0 | 0 | 0 | 0 | 0 | 0 | 0 | 0 | 0 | 0 |
| *S. aureus* | 50 | 55 | 35 | 45 | 20 | 40 | 20 | 25 | 10 | 15 | 5 | 10 | 0 | 0 |
| *S. pyogenes* | 40 | 60 | 30 | 35 | 25 | 35 | 15 | 20 | 10 | 10 | 5 | 10 | 0 | 0 |
| *C. perfringens* | 30 | 50 | 30 | 40 | 25 | 30 | 15 | 25 | 10 | 15 | 0 | 5 | 0 | 0 |
| *C. albicans* | 55 | 65 | 45 | 60 | 40 | 50 | 35 | 30 | 20 | 30 | 10 | 10 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs 30 ppm;
W-combination of plant extracts in water.

When suspended at a concentration of $10^4$ cells/ml (Table 12), under the influence of the extracts, all examined Gram-negative bacteria died within a shorter period of time—within 15 minutes. The quantities of tested Gram-positive microorganisms reduced more rapidly than when they were suspended at a concentration of $10^6$ cells/ml, however single *C. perfringens* cells remained viable for more than 60 minutes, and the others—for more than 2 hours in the presence of the extracts. The reduction of all microbial strains was quicker with AgNPs in the extract.

Conclusion

The tested extracts of African geranium (*Pelargonium sidoides* DC.) & black elderberry (*Sambucus nigra* L.), Saint John's Wort (*Hypericum perforatum* L.) & black elderberry (*Sambucus nigra* L.) and African geranium (*Pelargonium sidoides* DC.) & Saint John's Wort (*Hypericum perforatum* L.) showed a significant antimicrobial activity in vitro. The studied combinations had a synergetic effect against Gram-negative and Gram-positive microorganisms. The presence of colloidal nanosilver in the extracts and in the combination between them heightened their antimicrobial activity. This combination of extracts and AgNPs 30 ppm could be a reliable antimicrobial agent with a significant effect, in particular against Gram-negative bacteria, one of the most common causes of infection that is difficult to treat in humans and in animals. Among the Gram-positive micro-organisms, the obligate anaerobic bacterium *C. perfringens* and oval fungus *C. albicans* were more susceptible.

REFERENCES

Bauer, A. W., W. M. Kirby, J. C. Cherris, M. Truck. Antibiotic susceptibility testing by a standardized single disk method. The Am. J. of Clin. Pathol., 1966, 45, 4, 493-496.

Ericsson, H. M., J. S. Sherris. Antibiotic sensitivity testing. Acta Path. Microb. Scand. Suppl., 1971, 217, 3-86.

National Committee for Clinical Laboratory Standards: Performance Standards for Antimicrobial Disk Susceptibility Tests. 6-th ed. Approved Standard. NCCLS Document M2-A6, Vol. 17, No 1, 1997.

National Committee for Clinical Laboratory Standards: Performance Standards for Antimicrobial Susceptibility Testing: Ninths Informational Supplement. NCCLS Document M100-S9, Vol. 18, No 1, 1999.

Example 8: Complementary Study Protocol of the In Vitro Antimicrobial Activity of Extracts of African Geranium, Black Elderberry and Saint John's Wort in Colloidal Nanosilver The aim of this research work was to carry out studies to assess the in vitro antimicrobial activity of extracts of berries of *Pelargonium sidoides, Hypericum perforatum* and *Sambucus nigra*, alone or in combination with one another, in the form of colloidal nanosilver and in the form of aqueous extracts, against Gram-negative and Gram-positive microorganisms, which are among the most common causes of infection that is difficult to treat in humans and in animals.

Materials and Methods

Plant extracts. The antimicrobial effect of the aqueous African geranium (*Pelargonium sidoides* DC.), Saint John's Wort (*Hypericum perforatum* L.) and black elderberry (*Sambucus nigra* L.) extracts was tested. The same extracts were examined with nanoparticles of colloidal silver (AgNPs) at a concentration of 30 ppm.

Control. The broad spectrum antibiotic thiamphenicol (Nikovet-Sofia) was used as positive control, to which the tested microorganisms showed no resistance.

Microorganisms. Pure cultures of 7 pathogenic strains were tested. Five of them are references from Bulgaria's National Bank for Industrial Microorganisms and Cell Cultures (NBIMCC): *Esherichia coli* ATCC-8739 (NBIMCC 3397), *Salmonella enterica* subsp. *enterica* ATCC 1304 (NBIMCC 8691), *Staphylococcus aureus* subsp. *aureus* ATCC-6538 (NBIMCC 3359), *Clostridium perfringens* ATCC 13124 (NBIMCC 8615) and *Candida albicans* ATCC 10231 (NBIMCC 74). The other two (*Pseudomonas aeruginosa* and *Streptococcus pyogenes*) were isolated from dog inflammatory skin secretions in the microbiology laboratory of the university clinic of the University of Forestry, Faculty of Veterinary Medicine of Sofia.

Nutrient media. Mueller Hinton agar and broth (BUL BIO NCIPD-Sofia), Columbia blood agar (Biolab Zrt. H-1141, Budapest Ov. Utra 43), as well as selective media, were used: Endo agar (Antisel Sharlau Chemie S A, Spain) for *E. coli* and *S. enterica*, Cetrimide agar (Biolab Zrt. H-1141, Budapest Ov. Utr.) for *P. aeruginosa*, TSC *Perfringens agar* (MkB Test as, Slovakia), as well as Zeissler agar (BUL BIO NCIPD-Sofia) for *C. perfringens* and Sabouraud dextrose agar with chloramphenicol (Antisel Sharlau Chemie S A, Spain) for *C. albicans*.

The microorganisms were grown at 35-37° C. for 18-24 and 72 hours in an anaerobic environment for *C. perfringens* and in aerobic conditions for the other microbial species. The Anaerob Pack system with —H2+CO2 palladium catalyst (BUL BIO NCIPD-Sofia) in a jar was used to create anaerobic conditions. The Strip indicator (BUL BIO NCIPD-Sofia) was used to prove the creation of anaerobiosis.

The preliminary substance studies were performed using the standard method of diffusion on Bauer et al. agar (1966) and according to the National Committee for Clinical Laboratory Standards (NCCLS) M2-A3 (1997, 1999). Microorganism suspensions to be tested were inoculated in the exponential growth phase at a dose of $2 \cdot 10^6$ cells/ml in a volume of 0.1 ml in Petri dishes with a diameter of 9 cm on Zeissler agar for *C. perfringens* and Mueller-Hinton agar for the other microorganisms, with a pH of 7.2-7.4 and a layer thickness of 4 mm. 0.1 ml of plant extracts in colloidal silver and in water, as well as the control antibiotic, were applied in agar in 9 mm wells. The plant extracts, alone and in combination, respectively contained 2 mg of *P. sidoides*, 2 mg of *S. nigra*, 0.4 mg of *H. perforatum* and 24 ppm of AgNPs or water in 0.1 ml, and thiamphenicol—30 µg in 0.1 ml (as necessary). Following a 3-4 hour incubation period at room temperature for diffusion, the cultures were incubated at 35-37° C. for 18-24 and 72 hours. The results were read by measuring the diameters of the inhibitory zones in millimetres, including the well diameter to the nearest mm, using a transparent ruler outside the plate base. According to the three-stage Bauer-Kirby system, an inhibitory effect of the plant extracts with or without AgNPs was observed in zones>12 mm, and thiamphenicol at >17 mm. The susceptibility of the tested microorganisms was determined like for the non-antibiotic preparations such as sulfamides, namely: resistant (R) in zones with a diameter<12 mm, moderately susceptible intermediate (I) in zones between 13 and 16 mm and susceptible (S) at >17 mm. For thiamphenicol, the corresponding limits were as follows: R<12 mm, I—13-17 mm and S—>18 mm (NCCLS, 1997, 1999).

The minimum inhibitory concentrations (MIC) were determined using two-fold serial dilutions in Zeissler agar for *C. perfringens* and Mueller-Hinton agar for the other microorganisms, described by Ericsson and Sherris (1971) and NCCLS (1999). Bacterial suspensions were applied at a dose of $10^6$ cells/ml. The tested plant extracts of *P. sidoides, S. nigra* and *H. perforatum*, alone or in combination, in water or with AgNPs, as well as the control antibiotic, were administered at different doubly growing final concentrations per ml of agar. After incubating at 35-37° C. for 18-24 hours, the number of developed colonies was determined. The MIC50 were calculated mathematically based on the number of inhibited colonies on the agar with the respective dilution of the tested compound compared to the colonies on the media with controls without any plant extracts or antibiotic. The growth inhibition interval (D) was determined as the concentration without visible growth.

Determination of the antimicrobial action time of the aqueous plant extracts and those with colloidal nano silver. Each millilitre of extract contained 20 mg of *P. sidoides*, 20 mg of *S. nigra* and 4 mg of *H. perforatum*, respectively, and when the AgNPs were added, their final concentration was 24 ppm.

A suspension of each tested microbial strain with a concentration of $10^5$ cells/ml in a volume of 1 ml was added to 9 ml of the plant extract combination in water, as well as to 9 ml of aqueous extracts of each of these plants separately, where the final concentration became $10^4$ cells/ml. The same procedure was applied with the extracts containing AgNPs alone and separately.

A suspension of each microbial strain tested at a concentration of $10^7$ cells/ml in a volume of 1 ml was added to 9 ml of the plant extract combination, as well as to 9 ml of extracts of each of these plant extracts separately, where the final concentration of $10^6$ cells/ml was achieved. The same procedure was applied with the extracts containing AgNPs alone and separately.

The following controls were applied: sterile distilled water (without plant extracts and AgNPs) with the same content of each studied microbial strain, as well as a plant extract and AgNPs 30 ppm, without microorganisms.

After homogenization for 1 min on a Vortex apparatus (Heidolph-Labimex, Bulgaria) and different time intervals for the exposure of microorganisms to the tested plant extracts (1 min, 5 min, 15 min, 30 min, 60 min, 120 min, 2 h and 24 h), cultures were made from each sample on Zeissler agar for *C. perfringens* and on Mueller-Hinton agar for the other microorganisms, which were grown at 37° C. for 24-48 h in aerobic and anaerobic conditions. Following culture, the growth of the tested bacteria was reported and the number of developed colonies was determined.

All experiments were performed three times.

The findings were statistically processed using Student's and Fisher's standard method.

Findings

In the studies performed using the agar disk diffusion method, a strong inhibitory effect of the extracts of all the tested plants examined with AgNPs (inhibitory zone diameter between 16.0+0.6 and 24.3+1.3 mm) and the combination between them was reported (inhibitory zones between 18.3+3.3 and 28.7+3.1 mm) in all tested microorganisms. The summary data is shown in table 13. The effect of the combination of extracts of the three plants with AgNPs was greater than that with extracts with AgNPs applied separately. The differences in the mean inhibitory zone diameters (without microbial growth) between the individual plant extracts and the combination between them were not significant ($P>0.05$).

TABLE 13

Antimicrobial effect of the tested plant extracts with AgNPs tested alone and in combination with the Gram-positive and Gram-negative microorganisms with the agar-gel diffusion method.

| Microorganisms | Inhibitory zones in mm | | | | |
| --- | --- | --- | --- | --- | --- |
| | Combination | *P. sidoides* | *S. nigra* | *H. perforatum* | Thiamphenicol |
| *E. coli* | 28.7 ± 3.1 | 24.3 ± 1.3 | 23.7 ± 1.0 | 22.4 ± 0.8 | 36.0 ± 0.8 |
| *S. enterica* | 24.0 ± 5.8 | 21.8 ± 1.2 | 21.6 ± 0.9 | 20.7 ± 0.5 | 35.3 ± 0.8 |
| *P. aeruginosa* | 25.3 ± 4.2 | 23.0 ± 1.4 | 21.2 ± 1.4 | 21.5 ± 0.9 | 34.8 ± 0.8 |
| *S. aureus* | 20.7 ± 4.1 | 17.3 ± 1.0 | 17.6 ± 0.8 | 16.0 ± 0.6 | 25.7 ± 3.3 |
| *S. pyogenes* | 23.3 ± 6.7 | 21.3 ± 0.5 | 19.7 ± 0.6 | 20.7 ± 0.8 | 26.0 ± 4.5 |
| *C. perfringens* | 18.3 ± 3.3 | 16.9 ± 0.8 | 17.0 ± 0.8 | 16.3 ± 0.5 | 21.3 ± 0.5 |
| *C. albicans* | 21.7 ± 4.2 | 18.8 ± 0.8 | 19.2 ± 0.5 | 18.4 ± 0.5 | 28.7 ± 3.7 |
| Total Gram-negative | 25.9 ± 2.0 | 23.0 ± 1.3 | 22.2 ± 1.1 | 21.5 ± 0.7 | 35.4 ± 0.5 |
| Total Gram-positive | 20.8 ± 2.0 | 18.5 ± 3.1 | 18.1 ± 1.2 | 17.7 ± 2.1 | 24.3 ± 2.1 |
| Total bacteria | 23.3 ± 3.3 | 20.8 ± 2.8 | 20.1 ± 2.3 | 19.6 ± 2.5 | 29.9 ± 5.7 |
| Total (all microorganisms | 23.1 ± 3.1 | 20.5 ± 2.6 | 20.0 ± 2.2 | 19.4 ± 2.3 | 29.7 ± 5.3 |

The aqueous extracts of all the tested plants, as well as the combination between them (inhibitory zone diameters between 16.0+0.6 and 26.0+3.7 mm) also showed a high inhibitory effect on all tested microorganisms in the studies performed using the disk diffusion method. The results are shown in table 14. The effect of the combination between the extracts of the three plants was greater than that with extracts applied separately. The differences in the mean diameters of the non-growth zones between the individual plant extracts and the combination between them were not significant ($P>0.05$).

TABLE 14

Antimicrobial effect of the tested plant extracts with AgNPs tested alone and in combination with the Gram-positive and Gram-negative microorganisms with the agar-gel diffusion method.

| Microorganisms | Inhibitory zones in mm | | | | |
| --- | --- | --- | --- | --- | --- |
| | Combination | *P. sidoides* | *S. nigra* | *H. perforatum* | Thiamphenicol |
| *E. coli* | 26.0 ± 3.7 | 22.3 ± 1.2 | 21.9 ± 1.0 | 20.8 ± 0.8 | 36.0 ± 0.8 |
| *S. enterica* | 23.3 ± 1.7 | 20.7 ± 1.4 | 20.5 ± 1.9 | 20.0 ± 1.5 | 35.3 ± 0.8 |
| *P. aeruginosa* | 24.0 ± 2.4 | 21.7 ± 1.3 | 21.8 ± 2.4 | 19.5 ± 0.9 | 34.8 ± 0.8 |
| *S. aureus* | 18.7 ± 2.8 | 16.4 ± 0.8 | 17.0 ± 0.8 | 16.2 ± 0.7 | 25.7 ± 3.3 |
| *S. pyogenes* | 22.0 ± 4.8 | 23.3 ± 2.7 | 18.4 ± 0.6 | 20.7 ± 0.8 | 26.0 ± 4.5 |
| *C. perfringens* | 17.9 ± 3.5 | 17.2 ± 0.8 | 17.6 ± 0.8 | 16.3 ± 1.3 | 21.3 ± 0.5 |
| *C. albicans* | 20.7 ± 4.8 | 16.3 ± 0.9 | 15.9 ± 0.5 | 17.7 ± 1.5 | 28.7 ± 3.7 |
| Total Gram-negative | 24.4 ± 1.1 | 21.5 ± 0.8 | 21.4 ± 0.6 | 20.1 ± 0.5 | 35.4 ± 0.5 |
| Total Gram-positive | 19.5 ± 1.8 | 18.9 ± 3.1 | 17.7 ± 0.6 | 17.7 ± 2.1 | 24.3 ± 2.1 |
| Total bacteria | 22.0 ± 2.9 | 20.3 ± 2.6 | 19.5 ± 1.9 | 16.9 ± 1.9 | 29.9 ± 5.7 |
| Total (all microorganisms) | 21.8 ± 2.7 | 19.7 ± 2.8 | 19.0 ± 2.2 | 18.7 ± 1.8 | 29.7 ± 5.3 |

A slightly greater susceptibility to all the studied herbs, as well as to their combination, was shown by the tested Gram-negative bacteria compared to the Gram-positive microorganisms (P>0.05). The greatest susceptibility using this method was found in *E. coli* and *P. aeruginosa*. Fungus *C. albicans* also showed a susceptibility to all the studied herbs. All tested microorganisms showed high susceptibility to thiamphenicol, used as positive control. The differences in the diameters of the inhibitory zones of all the strains in the antibiotic and the studied extracts were statistically significant (P<0.05).

The results obtained during the determination of the minimum inhibitory concentrations (MIC) are shown in table 15. They correspond to those of the agar-gel diffusion method. The studied extracts of the three herbs showed a significant antimicrobial activity. The effect of *P. sidoides* and *S. nigra* was similar. Their MIC50 for the Gram-negative bacteria was low—10 mg/ml, and for the Gram-positive microorganisms—20 mg/ml. The growth of the studied microbial strains was inhibited by greater concentrations of *H. perforatum* 50 mg/ml for the Gram-negative strains and 100 mg/ml for the Gram-positive strains.

TABLE 15

Minimum inhibitory concentrations of the tested plant extracts in water against Gram-positive and Gram-negative microorganisms.

| Microorganisms | Minimum inhibitory concentrations in mg/ml | | | | | |
| | P. sidoides | | S. nigra | | H. perforatum | |
| | MICR | D | MIC50 | D | M1C5o | D |
| --- | --- | --- | --- | --- | --- | --- |
| *Escherichia coli* | 10 | 100 | 10 | 50 | 50 | 100 |
| *Salmonella enterica* | 10 | 100 | 10 | 50 | 50 | 100 |
| *Pseudomonas aeruginosa* | 10 | 100 | 10 | 50 | 50 | 100 |
| *Staphylococcus aureus* | 20 | 100 | 20 | 100 | 100 | 200 |
| *Streptococcus pyogenes* | 20 | 100 | 20 | 100 | 100 | 200 |
| *Clostridium perfringens* | 20 | 100 | 20 | 100 | 100 | 200 |
| *Candida albicans* | 20 | 100 | 20 | 100 | 100 | 200 |
| Total Gram-negative | 10.0 ± 0.0 | 100.0 ± | 10.0 ± 0.0 | 50.0 ± 0.0 | 50.0 ± 0.0 | 100.0 ± 0.0 |
| Total Gram-positive | 20.0 ± 0.0 | 100.0 ± 0.0 | 20.0 ± 0.0 | 100.0 ± 0.0 | 100.0 ± 0.0 | 200.0 ± 0.0 |
| Total bacteria | 15.0 ± 5.0 | 100.0 ± 0.0 | 15.0 ± 5.0 | 66.7 ± 37.3 | 66.7 ± 37.3 | 150.0 ± 50.0 |
| Total (all microorganisms) | 15.7 ± 4.9 | 100.0 ± 0.0 | 15.7 ± 4.9 | 78.6 ± 24.7 | 78.6 ± 24.7 | 157.1 ± 49.5 |

MIC50-growth inhibition at 50%;

D-total growth inhibition range

When applied in combination, these extracts showed a synergetic activity. The same antimicrobial effect was obtained at concentrations that were twice as low. The differences in MIC50 of *P. sidoides* and *S. nigra*, tested alone and in combination, were significant (P<0.01) in favour of the combination (the data is shown in table 2 of the previous protocol).

The data of the studies using the suspension method showed that the tested aqueous plant extracts, applied in combination, had a significant antimicrobial activity (Table 16). When the plant combination contained AgNPs, the bactericidal effect was quicker than without silver. As shown by the table data, when suspended with a concentration of $10^6$ cells/ml, the studied Gram-negative bacteria died rapidly—*E. coli* for 1 min with silver and up to 5 min without silver, *P. aeruginosa* respectively for 15-30 min, and *S. enterica* within 30 min. The plant extract combination also inactivated the Gram-positive microorganisms studied in a suspension with a concentration of $10^6$ cells/ml, however for a longer period of time—*C. perfringens* for 1 hour, and *S. aureus, S. pyogenes* and *C. albicans* for more than two hours. In the silver-free aqueous extracts, the reduction of tested microorganisms of all groups was slower than when the plant combination contained colloidal nanosilver.

TABLE 16

Antimicrobial effect of the tested plant extracts in combination with
AgNPs and in water against Gram-positive and Gram-negative microorganism
suspensions with a concentration of $10^6$ cells/ml

| | Strain growth (percentage of the number of colonies compared to the unprocessed controls) after different exposure intervals. | | | | | | | | | | | | | |
| | 1 min | | 5 min | | 15 min | | 30 min | | 60 min | | 120 min | | 24 h | |
| Microorganisms | Ag | W | Ag | W | Ag | W | Ag | W | Ag | W | Ag | W | Ag | W |
|---|---|---|---|---|---|---|---|---|---|---|---|---|---|---|
| E. coli | 0 | 10 | 0 | 0 | 0 | 0 | 0 | 0 | 0 | 0 | 0 | 0 | 0 | 0 |
| S. enterica | 10 | 20 | 5 | 10 | 0 | 5 | 0 | 0 | 0 | 0 | 0 | 0 | 0 | 0 |
| P. aeruginosa | 10 | 20 | 5 | 8 | 0 | 5 | 0 | 0 | 0 | 0 | 0 | 0 | 0 | 0 |
| S. aureus | 60 | 80 | 50 | 65 | 40 | 55 | 25 | 40 | 20 | 35 | 10 | 12 | 0 | 0 |
| S. pyogenes | 30 | 45 | 20 | 30 | 15 | 20 | 10 | 10 | 5 | 5 | 0 | 5 | 0 | 0 |
| C. perfringens | 25 | 35 | 15 | 25 | 10 | 20 | 5 | 8 | 0 | 0 | 0 | 0 | 0 | 0 |
| C. albicans | 60 | 70 | 50 | 60 | 25 | 35 | 20 | 30 | 20 | 20 | 5 | 8 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

When suspended at a concentration of $10^4$ cells/ml, the tested microorganisms showed greater susceptibility to the tested plant extracts applied in combination. Their quantities decreased more rapidly under the action of the means examined. When the plant combination contained AgNPs, its bactericidal effect was quicker than without silver. The results of this research are shown in table 17. In this experimental design, the tested Gram-negative bacteria died within a much shorter period of time. In the presence of nanosilver for 1 min, and without nanosilver—for 5 min. The plant extract combination also inactivated the Gram-positive microorganisms studied in a suspension with a concentration of $10^4$ cells/ml, however for a longer period of time—the anaerobe C. perfringens for 30 minutes, and the other bacterial species and the oval fungus C. albicans for more than two hours. As shown in the table data, in the silver-free aqueous extracts, the reduction of the tested microorganisms of all groups was slower than when the plant combination contained colloidal nanosilver.

TABLE 17

Antimicrobial effect of the P. sidoides extract with AgNPs and in
water against the Gram-positive and Gram-negative microorganisms in suspensions
with a concentration of $10^4$ cells/ml

| | Strain growth (percentage of the number of colonies compared to the unprocessed controls) after different exposure intervals. | | | | | | | | | | | | | |
| | 1 min | | 5 min | | 15 min | | 30 min | | 60 min | | 120 min | | 24 h | |
| Microorganisms | Ag | W | Ag | W | Ag | W | Ag | W | Ag | W | Ag | W | Ag | W |
|---|---|---|---|---|---|---|---|---|---|---|---|---|---|---|
| E. coli | 0 | 8 | 0 | 0 | 0 | 0 | 0 | 0 | 0 | 0 | 0 | 0 | 0 | 0 |
| S. enterica | 0 | 6 | 0 | 0 | 0 | 0 | 0 | 0 | 0 | 0 | 0 | 0 | 0 | 0 |
| P. aeruginosa | 0 | 5 | 0 | 0 | 0 | 0 | 0 | 0 | 0 | 0 | 0 | $0_1$ | 0 | 0 |
| S. aureus | 40 | 58 | 30 | 45 | 25 | 30 | 20 | 25 | 10 | 10 | 5 | 6 | 0 | 0 |
| S. pyogenes | 25 | 30 | 20 | 25 | 10 | 15 | 5 | 10 | 0 | 5 | 0 | 5 | 0 | 0 |
| C. perfringens | 20 | 30 | 10 | 20 | 5 | 10 | 0 | 0 | 0 | 0' | 0 | 0 | 0 | 0 |
| C. albicans | 45 | 50 | 30 | 35 | 15 | 20 | 10 | 15 | 5 | 10 | 0 | 5 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

The results of the studies of the African geranium (P. sidoides) extract using the suspension method are shown in tables 18 and 19. The plant extract showed significant antimicrobial activity, which increased with the addition of colloidal nanosilver. The studied Gram-negative bacteria suspensions with a concentration of $10^6$ cells/ml died within quite a short period of time—E. coli up to 5 minutes with nanosilver and up to 15 min without silver, and S. enterica and P. aeruginosa—within 15 min with silver and 30 min without nanosilver. The P. sidoides extract inactivated the studied Gram-positive microorganisms, however for a longer period of time—C. perfringens for more than one hour, and the other bacterial species and fungus C. albicans for more than two hours.

TABLE 18

Antimicrobial effect of the *P. sidoides* extract with AgNPs and with
water against the Gram-positive and Gram-negative microorganisms in suspensions
with a concentration of $10^6$ cells/ml Strain growth (percentage of the number of colonies compared to the
unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 15 | 10 | 0 | 5 | 0 | 0 | 0 | 0 | 0 | 0 | 0 | 0 | 0 | 0 |
| *S. enterica* | 12 | 15 | 0 | 10 | 0 | 5 | 0 | 0 | 0 | 0 | 0 | 0 | 0 | 0 |
| *P. aeruginosa* | 15 | 18 | 5 | 8 | 0 | 5 | 0 | 0 | 0 | 0 | 0 | 0 | 0 | 0 |
| *S. aureus* | 70 | 85 | 60 | 70 | 45 | 60 | 30 | 45 | 20 | 35 | 16 | 20 | 0 | 0 |
| *S. pyogenes* | 60 | 75 | 50 | 60 | 35 | 40 | 20 | 30 | 15 | 25 | 5 | 10 | 0 | 0 |
| *C. perfringens* | 45 | 55 | 30 | 45 | 20 | 30 | 10 | 20 | 6 | 10 | 0 | 0 | 0 | 0 |
| *C. albicans* | 69 | 80 | 55 | 70 | 45 | 55 | 30 | 38 | 20 | 25 | 10 | 10 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

TABLE 19

Antimicrobial effect of the *P. sidoides* extract with AgNPs and with
water against the Gram-positive and Gram-negative microorganisms in suspensions
with a concentration of cells/ml Strain growth (percentage of the number of colonies compared to the
unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 15 | 10 | 0 | 0 | 0 | 0 | 0 | 0 | 0 | 0 | 0 | 0 | 0 | 0 |
| *S. enterica* | 10 | 10 | 0 | 5 | 0 | 0 | 0 | 0 | 0 | 0 | 0 | 0 | 0 | 0 |
| *P. aeruginosa* | 5 | 10 | 0 | 5 | 0 | 0 | 0 | 0 | 0 | 0 | 0 | 0 | 0 | 0 |
| *S. aureus* | 50 | 65 | 40 | 50 | 30 | 40 | 20 | 30 | 15 | 20 | 8 | 10 | 0 | 0 |
| *S. pyogenes* | 45 | 60 | 30 | 45 | 20 | 35 | 15 | 20 | 10 | 15 | 0 | 8 | 0 | 0 |
| *C. perfringens* | 35 | 50 | 25 | 40 | 15 | 20 | 10 | 15 | 0 | 0 | 0 | 0 | 0 | 0 |
| *C. albicans* | 60 | 75 | 50 | 60 | 35 | 45 | 20 | 35 | 10 | 20 | 5 | 10 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

When suspended with a concentration of $10^4$ cells/ml (Table 19) under the influence of the *P. sidoides* extract, the Gram-negative bacteria died within a shorter period of time—*E. coli* within 5 min, and *S. enterica* and *P. aeruginosa*—within less than 5 min with nanosilver and up to 15 min without silver. The quantities of Gram-positive microorganisms reduced more rapidly than when they were in a suspension with a greater concentration, however single *C. perfringens* cells remained viable for more than 30 minutes, and the others for more than 2 hours in the presence of this extract.

Tables 20 and 21 show the test results in the suspension method of the black elderberry (*S. nigra*) berry extract. All the Gram-negative bacteria tested in a suspension with a concentration of $10^6$ cells/ml died within 30 min, however much more rapidly when the extract contained nanosilver. The *S. nigra* berry extract also inactivated the Gram-positive microorganisms studied in a suspension with a concentration of $10^6$ cells/ml, however for a longer period of time—*C. perfringens* for 2 hours, and the other bacterial species and the oval fungus *C. albicans* for more than two hours (Table 20). For the *S. nigra* berry extract containing silver, the reduction of the tested microorganisms of all groups was quicker compared to the aqueous extract.

TABLE 20

Antimicrobial effect of the *S. nigra* extract with AgNPs 30 ppm and with water against the Gram-positive and Gram-negative microorganisms in suspensions with a concentration of $10^6$ cells/ml.

Strain growth (percentage of the number of colonies compared to the unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 10 | 10 | 0 | 5 | 0 | 0 | 0 | 0 | 0 | 0 | 0 | 0 | 0 | 0 |
| *S. enterica* | 10 | 16 | 0 | 10 | 0 | 5 | 0 | 0 | 0 | 0 | 0 | 0 | 0 | 0 |
| *P. aeruginosa* | 15 | 18 | 8 | 10 | 0 | 6 | 0 | 0 | 0 | 0 | 0 | 0 | 0 | 0 |
| *S. aureus* | 75 | 85 | 60 | 75 | 50 | 60 | 40 | 48 | 30 | 35 | 20 | 25 | 0 | 0 |
| *S. pyogenes* | 70 | 80 | 60 | 70 | 45 | 55 | 30 | 35 | 20 | 20 | 8 | 10 | 0 | 0 |
| *C. perfringens* | 60 | 65 | 45 | 50 | 30 | 38 | 20 | 26 | 15 | 20 | 0 | 0 | 0 | 0 |
| *C. albicans* | 70 | 80 | 60 | 68 | 50 | 55 | 38 | 45 | 22 | 30 | 15 | 20 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

When suspended with a concentration of $10^4$ cells/ml under the influence of the *S. nigra* berry extract (Table 21), the Gram-negative bacteria died within a shorter period of time—up to 15 min. The quantities of Gram-positive microorganisms decreased more rapidly than when in a suspension at a concentration of $10^6$ cells/ml, however single *C. perfringens* cells remained viable for more than 30 minutes and the others—for more than 2 hours under the influence of this extract. The presence of nanosilver in the extract led to a quicker microbial cell reduction.

TABLE 21

Antimicrobial effect of the *S. nigra* extract with AgNPs 30 ppm and with water against the Gram-positive and Gram-negative microorganisms in suspensions with a concentration of $10^4$ cells/ml.

Strain growth (percentage of the number of colonies compared to the unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 18 | 20 | 10 | 15 | 0 | 0 | 0 | 0 | 0 | 0 | 0 | 0 | 0 | 0 |
| *S. enterica* | 20 | 25 | 15 | 18 | 0 | 0 | 0 | 0 | 0 | 0 | 0 | 0 | 0 | 0 |
| *P. aeruginosa* | 15 | 20 | 8 | 15 | 0 | 0 | 0 | 0 | 0 | 0 | 0 | 0 | 0 | 0 |
| *S. aureus* | 55 | 70 | 50 | 60 | 40 | 48 | 25 | 30 | 16 | 22 | 10 | 15 | 0 | 0 |
| *S. pyogenes* | 48 | 65 | 35 | 50 | 25 | 30 | 18 | 25 | 13 | 18 | 5 | 10 | 0 | 0 |
| *C. perfringens* | 42 | 58 | 35 | 45 | 18 | 28 | 12 | 20 | 5 | 10 | 0 | 0 | 0 | 0 |
| *C. albicans* | 65 | 78 | 55 | 62 | 40 | 50 | 30 | 38 | 20 | 30 | 10 | 20 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

The results of the tests of the yellow Saint John's Wort (*H. perforatum*) extract against the microbial suspensions are shown in tables 22 and 23. This extract also showed a significant antimicrobial activity, in particular with colloidal nanosilver. The studied Gram-negative bacteria died within a short period of time—15 minutes with silver, and within a slightly longer period of time without silver. The *H. perforatum* extract inactivated the Gram-positive microorganisms studied in a suspension with a concentration of $10^6$ cells/ml, however for a longer period of time—*C. perfringens* for 2 hours, and the other bacterial species and *C. albicans*—for more than two hours. With nanosilver in the extract, a quicker reduction of all microbial cell types was achieved.

TABLE 22

Antimicrobial effect of the *H. perforatum* extract with AgNPs 30 ppm
and with water against Gram-positive and Gram-negative microorganisms in
suspensions with a concentration of $10^6$ cells/ml Strain growth (percentage of the number of colonies compared
to the unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 10 | 12 | 0 | 8 | 0 | 0 | 0 | 0 | 0 | 0 | 0 | 0 | 0 | 0 |
| *S. enterica* | 8 | 15 | 0 | 10 | 0 | 5 | 0 | 0 | 0 | 0 | 0 | 0 | 0 | 0 |
| *P. aeruginosa* | 16 | 20 | 8 | 10 | 0 | 5 | 0 | 0 | 0 | 0 | 0 | 0 | 0 | 0 |
| *S. aureus* | 72 | 80 | 65 | 78 | 55 | 63 | 45 | 50 | 35 | 38 | 15 | 20 | 0 | 0 |
| *S. pyogenes* | 65 | 72 | 50 | 65 | 40 | 58 | 33 | 40 | 20 | 25 | 10 | 15 | 0 | 0 |
| *C. perfringens* | 58 | 70 | 40 | 57 | 32 | 40 | 25 | 30 | 18 | 22 | 0 | 0 | 0 | 0 |
| *C. albicans* | 75 | 80 | 62 | 70 | 48 | 60 | 35 | 50 | 20 | 37 | 10 | 18 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

TABLE 23

Antimicrobial effect of the *H. perforatum* extract with AgNPs 30 ppm
and with water against Gram-positive and Gram-negative microorganisms in
suspensions with a concentration of $10^4$ cells/ml Strain growth (percentage of the number of colonies compared to the
unprocessed controls) after different exposure intervals.

| Microorganisms | 1 min | | 5 min | | 15 min | | 30 min | | 60 min | | 120 min | | 24 h | |
|---|---|---|---|---|---|---|---|---|---|---|---|---|---|---|
| | Ag | W | Ag | W | Ag | W | Ag | W | Ag | W | Ag | W | Ag | W |
| *E. coli* | 15 | 22 | 8 | 15 | 0 | 0 | 0 | 0 | 0 | 0 | 0 | 0 | 0 | 0 |
| *S. enterica* | 25 | 30 | 12 | 20 | 0 | 0 | 0 | 0 | 0 | 0 | 0 | 0 | 0 | 0 |
| *P. aeruginosa* | 18 | 25 | 10 | 15 | 0 | 0 | 0 | 0 | 0 | 0 | 0 | 0 | 0 | 0 |
| *S. aureus* | 62 | 78 | 45 | 60 | 30 | 50 | 22 | 35 | 15 | 20 | 8 | 12 | 0 | 0 |
| *S. pyogenes* | 55 | 70 | 40 | 55 | 35 | 40 | 20 | 28 | 12 | 15 | 10 | 15 | 0 | 0 |
| *C. perfringens* | 50 | 60 | 42 | 50 | 30 | 40 | 20 | 32 | 10 | 20 | 0 | 0 | 0 | 0 |
| *C. albicans* | 76 | 80 | 65 | 70 | 50 | 55 | 42 | 50 | 30 | 38 | 20 | 20 | 0 | 0 |
| Unprocessed controls | 100 | 100 | 100 | 100 | 100 | 100 | 100 | 100 | 100 | 100 | 100 | 100 | 100 | 100 |

Ag-combination of plant extracts with AgNPs;
W-combination of plant extracts in water.

When suspended with a concentration of $10^4$ cells/ml under the influence of *H. perforatum*, all examined Gram-negative bacteria died within a shorter period of time—within 15 minutes. The quantities of tested Gram-positive microorganisms reduced more rapidly than when they were suspended at a concentration of $10^6$ cells/ml, however single *S. pyogenes* and *C. perfringens* cells remained viable for more than 60 minutes, and the others—for more than 2 hours, with the *H. perforatum* extract. The reduction of all microbial strains was quicker with AgNPs in the extract.

CONCLUSIONS

The tested *Pelargonium sidoides, Hypericum perforatum* and *Sambucus nigra* berry extracts showed a significant in vitro antimicrobial activity both alone and in combination. The studied combination of the three extracts had a synergetic effect against the Gram-negative and Gram-positive microorganisms. The presence of colloidal nanosilver in the extracts and in the combination between them heightened their antimicrobial activity. This combination of extracts and AgNPs 30 ppm could be a reliable antimicrobial agent with a significant effect, in particular against Gram-negative bacteria, one of the most common causes of infection that is difficult to treat in humans and in animals. Among the Gram-positive microorganisms, the obligate anaerobic bacterium *C. perfringens* and oval fungus *C. albicans* were more susceptible.

The invention claimed is:

1. Formulation for use as a drug, comprising:
   between 20 and 250 mg of total silver per litre of formulation, distributed as:
   i. between 70 and 99.99% by total weight of colloidal silver;
   ii. between 0.01 and 30% by total weight of ionic silver;
   between 0.3 and 5% by weight of *Sambucus nigra* extract;
   between 1 and 9% by weight of *Primulae flos* cum calycibus extract and/or *Hypericum perforatum* extract; and
   between 1 and 6% by weight of *Pelargonium sidoides* extract.

2. Formulation for use as a drug, according to claim 1, characterized in that said colloidal silver has a particle size between 0.1 and 30 nanometres.

3. Formulation for use as a drug according to claim 1, further comprising:

*Echinacea* extract, and/or

*Propolis* and/or

*Artemisia* extract and/or

*Allium sativum* extract.

4. Formulation for use as a drug according to claim 3, comprising:

Between 0.01 and 8% by weight of the *Echinacea* extract, and/or

Between 0.01 and 7% by weight of the *Propolis*, and/or

Between 0.5 and 3% by weight of the *Artemisia* extract, and/or

Between 0.01 and 10% by weight of the *Allium sativum* extract.

5. Formulation for use as a drug according to claim 1, characterised in that it is in a form suitable for oral, intravenous, subcutaneous, nasal, ophthalmic, auricular, rectal, vaginal, respiratory routes of administration or application on the skin.

6. Formulation for use as a drug according to claim 5, characterized in that the route of application on the skin is an ointment, cream, patch or gel.

7. Formulation for use as a drug according to claim 6, designed for use for antifungal and antibacterial treatment, by application on the skin as a cream.

8. Formulation for use as a drug according to claim 6, designed for use for antifungal treatment, by application on the skin as a cream.

9. Formulation for use as a drug according to claim 6, designed for use for antibacterial treatment, by application on the skin as a cream.

10. Formulation for use as a drug according to claim 1, designed for use for antiviral, antibacterial and antifungal treatment.

11. Formulation for use as a drug according to claim 1, designed for use as an antibiotic.

12. Formulation for use as a drug according to claim 11, designed for use in antibiotic-resistant patients.

\* \* \* \* \*